(12) United States Patent
Carle et al.

(10) Patent No.: US 10,869,821 B2
(45) Date of Patent: *Dec. 22, 2020

(54) TOPICAL SKIN FORMULATIONS

(71) Applicant: Mary Kay Inc., Addison, TX (US)

(72) Inventors: Tiffany Carle, Addison, TX (US); Bob Foley, Addison, TX (US); Julia Collier, Addison, TX (US); Wanli Zhao, Addison, TX (US); Geetha Kalahasti, Addison, TX (US)

(73) Assignee: Mary Kay Inc., Addison, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/232,723

(22) Filed: Dec. 26, 2018

(65) Prior Publication Data
US 2019/0133923 A1    May 9, 2019

Related U.S. Application Data

(63) Continuation of application No. 16/037,180, filed on Jul. 17, 2018, now Pat. No. 10,201,495, which is a continuation of application No. 15/606,683, filed on May 26, 2017, now Pat. No. 10,052,278, which is a continuation of application No. 15/218,840, filed on Jul. 25, 2016, now Pat. No. 9,687,442.

(60) Provisional application No. 62/197,232, filed on Jul. 27, 2015.

(51) Int. Cl.
| | | |
|---|---|---|
| *A61K 36/00* | (2006.01) | |
| *A61K 8/34* | (2006.01) | |
| *A61Q 19/00* | (2006.01) | |
| *A61Q 1/02* | (2006.01) | |
| *A61Q 19/10* | (2006.01) | |
| *A61K 8/73* | (2006.01) | |
| *A61K 8/60* | (2006.01) | |
| *A61K 8/9717* | (2017.01) | |
| *A61K 8/02* | (2006.01) | |

(52) U.S. Cl.
CPC ........... *A61K 8/345* (2013.01); *A61K 8/0212* (2013.01); *A61K 8/34* (2013.01); *A61K 8/60* (2013.01); *A61K 8/73* (2013.01); *A61K 8/9717* (2017.08); *A61Q 1/02* (2013.01); *A61Q 19/00* (2013.01); *A61Q 19/007* (2013.01); *A61Q 19/10* (2013.01); *A61K 2800/59* (2013.01)

(58) Field of Classification Search
CPC .................................................... A61K 36/00
USPC ....................................................... 424/725
See application file for complete search history.

(56) References Cited

U.S. PATENT DOCUMENTS

| | | |
|---|---|---|
| 2,789,053 A | 7/1957 | Brown |
| 3,755,560 A | 8/1973 | Dickert et al. |
| 4,421,769 A | 12/1983 | Dixon et al. |
| 4,509,949 A | 4/1985 | Huang et al. |
| 4,599,379 A | 7/1986 | Flesher et al. |
| 4,628,078 A | 12/1986 | Glover et al. |
| 4,835,206 A | 5/1989 | Farrar et al. |
| 4,849,484 A | 7/1989 | Heard |
| 5,011,681 A | 4/1991 | Ciotti et al. |
| 5,084,270 A | 1/1992 | Ciaudelli |
| 5,087,445 A | 2/1992 | Haffey et al. |
| 5,100,660 A | 3/1992 | Hawe et al. |
| 6,328,987 B1 | 12/2001 | Marini |
| 2006/0074029 A1 | 4/2006 | Leece |
| 2011/0124544 A1 | 5/2011 | He et al. |
| 2013/0017239 A1 | 1/2013 | Viladot et al. |
| 2013/0216596 A1 | 8/2013 | Viladot et al. |

FOREIGN PATENT DOCUMENTS

| | | |
|---|---|---|
| CN | 1473855 A | 2/2004 |
| CN | 101357113 | 2/2009 |
| CN | 101528194 | 9/2009 |
| CN | 10164779 | 2/2010 |
| CN | 101801391 A | 8/2010 |
| CN | 102083408 A | 6/2011 |
| CN | 102177253 | 9/2011 |
| CN | 102400538 | 4/2012 |
| CN | 102475665 | 5/2012 |
| CN | 102920631 A | 2/2013 |
| CN | 10376482 A | 4/2014 |
| EP | 2827837 B1 | 3/2020 |
| FR | 2957923 | 9/2011 |
| JP | 2005298504 | 10/2005 |
| KR | 10-1607235 | 3/1916 |
| KR | 10--0798607 | 1/2008 |
| KR | 10-2009-0098126 | 10/2009 |

(Continued)

OTHER PUBLICATIONS

Anonymous, "Exossine™ Exotic Multifunctional Line Purified exopolysaccharides synthesized by Kopara Microorganisms" Mar. 30, 2012, p. e1-e6, Retrieved from the Internet URL: < http://cdn.shopify.com/s/files/1/0319/8073/files/Exossine_Exo-T_Exo-P.pdf >.

Anonymous, "Face and Body Care" Nov. 14, 2013, pp. e1-e4, Retrieved from the Internet URL: < http://www.corneliusrussia.ru/Downloads/12112013154648Greentech%20Product%Brochure/$file/GREENTECH%product%20catalogue.pdf >.

Anonymous, "How to find your active" Mar. 23, 2012, p. e1, Retrieved from the Internet URL: < http://api.respharma.com/Brochure/GREENTECH//0-Fine_your_active_FR-GC_BD.pdf >.

(Continued)

*Primary Examiner* — Michael V Meller
(74) *Attorney, Agent, or Firm* — Norton Rose Fulbright US LLP

(57) ABSTRACT

A method of treating skin is disclosed. The method can include topically applying to a peron's skin a composition comprising 0.0001% to 5% w/w of a hydrolyzed algae extract comprising exopolysaccharides from *Halymenia durvillei*, and 0.0001% to 5% w/w of a saccharide isomerate comprising an exopolysaccharide synthesized by *Vibrio alginolyticus*, wherein at least one of skin permeability is decreased, filaggrin production is increased, skin moisture is increased, occludin production is increased, or TNFα production is inhibited in the skin.

10 Claims, No Drawings

(56) References Cited

FOREIGN PATENT DOCUMENTS

| KR | 10-2013-7026407 | 10/2013 |
|----|----|----|
| KR | 10-137213 | 3/2014 |
| KR | 10-139396 | 6/2014 |
| KR | 10-1414734 | 6/2014 |
| KR | 10-510575 | 4/2015 |
| WO | WO 2009/125182 | 10/2009 |
| WO | WO 2009/127057 | 10/2009 |
| WO | WO 2011/117547 | 9/2011 |
| WO | WO 2013/139965 | 9/2013 |
| WO | WO 2013/149323 | 10/2013 |

OTHER PUBLICATIONS

Extended Search Report issued in European Patent Application No. 16831197, dated Jan. 2, 2019.
Specialchem: "Greentech Presented Solutions to Combat Skin Problems at in-cosmetics 2012" May 23, 2012, pp. e1-e2, Retrieved from the Internet, URL: <https://cosmetics.specialchem.com/new/products-new/greentech-presented-solutions-to-combat-skin-problems-at-incosmetics-2012>.
"Hydrolyzed Algae Extract," *International Cosmetic Ingredient Dictionary and Handbook, CTFA*, $12^{th}$ ed., 2008, p. 1211.
"Saccharide Isomerase," *International Cosmetic Ingredient Dictionary and Handbook, CTFA*, $12^{th}$ ed., 2008, p. 2409.
International Search Report and Written Opinion issued for Application No. PCT/US2016/043878, dated Oct. 21, 2016.
The First Office Action from the China National Intellectual Property Administration issued in corresponding Application No. 201680052997.2 dated Jul. 9, 2020.
Search Report from the China National Intellectual Property Administration issued in corresponding Application No. 2016800529972 dated Jul. 2, 2020.
Zhai et al., *Cytobiology*, $4^{th}$ Edition, Higher Education Press, pp. 361-32, 2011.
Zhong et al, *New Vascular Eye Disease*, People's Military Doctor Press, p. 87, 2006.
Chaisemartin et al., "Marine exploration", *Soap, Perfumery & Cosmetics*, pp. 30-33, 2010.

TOPICAL SKIN FORMULATIONS

CROSS-REFERENCE TO RELATED APPLICATIONS

This application is a continuation of U.S. application Ser. No. 16/037,180, filed Jul. 17, 2018, which is a continuation of U.S. application Ser. No. 15/606,683, filed May 26, 2017 (issued as U.S. Ser. No. 10/052,278), which is a continuation of U.S. application Ser. No. 15/218,840, filed Jul. 25, 2016 (issued as U.S. Pat. No. 9,687,442), which claims the benefit of U.S. Provisional Application No. 62/197,232 filed Jul. 27, 2015. The contents of the referenced applications are incorporated into the present application by reference.

BACKGROUND OF THE INVENTION

A. Field of the Invention

The present invention relates generally to the field of cosmetics. More particularly, it concerns compositions that can be used to exfoliate, moisturize, or prepare skin for moisturization. In another aspect, the composition can be used as a cleanser or freshener to remove residue, dirt, oil, grease, tars, etc., from surfaces. In yet another aspect, the composition can be used as a cosmetic foundation.

B. Description of Related Art

Ageing, chronic exposure to adverse environmental factors, malnutrition, fatigue, etc., can change the visual appearance, physical properties, or physiological functions of skin in ways that are considered visually undesirable. The most notable and obvious changes include the development of fine lines and wrinkles, loss of elasticity, increased sagging, loss of firmness, loss of color evenness or tone, coarse surface texture, and mottled pigmentation. Less obvious but measurable changes which occur as skin ages or endures chronic environmental insult include a general reduction in cellular and tissue vitality, reduction in cell replication rates, reduced cutaneous blood flow, reduced moisture content, accumulated errors in structure and function, alterations in the normal regulation of common biochemical pathways, and a reduction in the skin's ability to remodel and repair itself. Many of the alterations in appearance and function of the skin are caused by changes in the outer epidermal layer of the skin, while others are caused by changes in the lower dermis.

Previous attempts to improve the visual appearance of skin with known skin active-ingredients have been shown to have various drawbacks such as skin irritation and prolonged recovery periods.

Maintaining moisture of the skin and/or hair helps overcome some unwanted changes in skin and hair. However, maintaining moisture of the skin can be difficult. This is especially true for subjects with skin that is more dry than average (dry skin type). Exposure to chemicals, solvents, washing, cosmetics, fabrics, or dry environments are some of the many ways that skin can lose moisture.

Skin and hair can lose moisture as a result of cleansing and/or freshening the skin and hair. Skin and hair cleansing and/or freshening compositions are typically applied to skin and/or hair and rinsed-off with water (e.g., rinse-off product), robbing the skin of natural oils and lipids. Further, cleansing and freshening compositions oftentimes have ingredients that can be caustic to the surfaces to be cleansed. For instance, many types of cleansers and fresheners use certain surfactants that can cause skin irritation.

Cosmetics, including makeup foundations and masks, can cause drying of the skin. Foundations are typically applied to skin and left on the skin so that additional makeup may be applied or to hide the appearance of unwanted blemishes or colors. Some problems associated with foundations include skin irritation, stability, lack of adequate effectiveness, difficulty in applying to skin, and drying of the skin. Masks are typically applied to skin and left on the skin for a period of time to allow the claimed benefits of the mask to occur. Problems associated with masks include skin irritation, stability, lack of adequate effectiveness, difficulty in applying to skin, and drying of the skin. Many masks also exfoliate the skin, which can cause or exasperate irritation, sensitivity, and dryness.

Moisturizers are complex mixtures of chemical agents specially designed to make the external layers of the skin (epidermis) softer and more pliable. They increase the skin's hydration (water content) by reducing evaporation. Naturally occurring skin lipids and sterols, as well as artificial or natural oils, humectants, emollients, lubricants, etc., may be part of the composition of commercial skin moisturizers. They usually are available as commercial products for cosmetic and therapeutic uses, but can also be made at home using common pharmacy ingredients. However, moisturizers are not perfect. Some problems associated with moisturizers include unpleasant tactile properties (e.g., heavy, greasy, or sticky feel), instability, skin-irritation, or insufficient moisturization capabilities.

SUMMARY OF THE INVENTION

The inventors determined that a combination of compounds, compositions, and extracts that have therapeutic benefits. In particular, the inventors identified a combination of ingredients, including hydrolyzed algae extract and saccharide isomerate, that work to moisturize and/or improve the appearance and/or condition of skin and/or hair. In particular aspects, the saccharide isomerate may contain an exopolysaccharide synthesized by *Vibrio alginolyticus*, capable of increasing production of filaggrin, increasing skin moisture, increasing production of occluding, inhibiting TNFα production, and/or preventing oxidative damage. In particular aspects, the hydrolyzed algae extract contains exopolysaccharides of *Halymenia durvillei* and is capable of increasing production of filaggrin, increasing skin moisture, increasing production of occludin, and/or decreasing skin permeability. The present invention overcomes deficiencies in the art by providing stable moisturizer, mask, foundation, freshener, and cleanser compositions that can also effectively decrease skin permeability, increase filaggrin production, increase skin moisture, increase occludin production, inhibit TNFα production, and prevent oxidative damage.

In some embodiments, there is disclosed a topical composition. In some aspects, the topical composition includes any one of, any combination of, or all of hydrolyzed algae extract, saccharide isomerate, and a dermatologically acceptable vehicle. The amounts of the ingredients within the composition can vary (e.g., amounts can be as low as 0.000001% to as high as 98% w/w or any range therein). In some aspects, the composition contains an effective amount of saccharide isomerate capable of increasing production of filaggrin, increasing skin moisture, increasing production of occluding, inhibiting TNFα production, and/or preventing oxidative damage. In some aspects, the composition contains an effective amount of hydrolyzed algae extract capable of increasing production of filaggrin, increasing skin moisture, increasing production of occludin, and/or decreasing skin permeability. In some aspects, the saccharide isomerate is an exopolysaccharide synthesized by *Vibrio*

*alginolyticus*. In some aspects, the hydrolyzed algae extract comprises exopolysaccharides of *Halymenia durvillei*. In some aspects, the composition includes: 0.001% to 1% w/w of hydrolyzed algae extract and 0.0001% to 0.1% w/w of saccharide isomerate. In some aspects, the composition is formulated as at least one of a moisturizer, a mask, a foundation, a freshener, and/or a cleanser. In some aspects, the dermatologically acceptable vehicle can contain water, or can be water. In some aspects, the composition contains 35% to 98% w/w of water. In some aspects, the composition further contains glycerin and phenoxyethanol. In some aspects, the composition includes 1% to 15% w/w of glycerin and 0.1% to 1.5% w/w of phenoxyethanol. The composition may further comprise one or more ingredients described herein. For example, the composition may comprise one or more additional ingredients selected from one or more conditioning agents, moisturizing agents, pH adjusters, structuring agents, inorganic salts, and preservatives. In some aspects, the composition is capable of moisturizing skin and/or hair. In some aspects, the composition is capable of moisturizing dry skin and/or dry hair.

In another aspect, disclosed is a moisturizer composition. In some aspects, the topical composition above further includes any one of, any combination of, or all of cyclopentasiloxane, hydrogenated polyisobutene, butylene glycol, dimethicone, octyldodecyl myristate, arachidyl alcohol, glyceryl stearate, cetearyl alcohol, petrolatum, and PEG-100 stearate. The amounts of the ingredients within the composition can vary (e.g., amounts can be as low as 0.000001% to as high as 98% w/w or any range therein). In some aspects, the composition includes: 1% to 10% w/w of cyclopentasiloxane, 1% to 10% w/w of hydrogenated polyisobutene, 1% to 10% w/w of butylene glycol, 1% to 10% w/w of dimethicone, 0.5% to 5% w/w of octyldodecyl myristate, 0.5% to 5% w/w of arachidyl alcohol, 0.5% to 5% w/w of glyceryl stearate, 0.1% to 3% w/w of cetearyl alcohol, 0.1% to 3% w/w of petrolatum, and 0.1% to 3% w/w of PEG-100 stearate. In some aspects, the composition further includes: behenyl alcohol, ammonium acryloyldimethyltaurate/VP copolymer, arachidyl glucoside, dimethicone/vinyl dimethicone crosspolymer, chlorphenesin, and disodium EDTA. In some aspects, the composition includes 0.1% to 3% w/w of behenyl alcohol, 0.1% to 1.5% w/w of ammonium acryloyldimethyltaurate/VP copolymer, 0.1% to 1.5% w/w of arachidyl glucoside, 0.1% to 1% w/w of dimethicone/vinyl dimethicone crosspolymer, 0.05% to 0.5% w/w of chlorphenesin, and 0.01% to 0.5% w/w of disodium EDTA. In some aspects, the composition further includes *Opuntia tuna* fruit extract. In some aspects, the composition includes 0.0001% to 0.1% w/w of *Opuntia tuna* fruit extract. In some aspects, the composition is formulated as a moisturizer.

In yet another aspect, disclosed is a mask. In some aspects, the topical composition above further includes any one of, any combination of, or all of glyceryl stearate, petrolatum, stearic acid, cetyl alcohol, lauryl methacrylate/glycol dimethacrylate crosspolymer, and stearyl alcohol. The amounts of the ingredients within the composition can vary (e.g., amounts can be as low as 0.000001% to as high as 98% w/w or any range therein). In some aspects, the composition includes: 1% to 10% w/w of glyceryl stearate, 1% to 10% w/w of petrolatum, 0.5% to 5% w/w of stearic acid, 0.5% to 5% w/w of cetyl alcohol, 0.1% to 3% w/w of lauryl methacrylate/glycol dimethacrylate crosspolymer, and 0.1% to 3% w/w of stearyl alcohol. In some aspects, the composition includes: triethanolamine, dimethicone, titanium dioxide, betaine, carbomer, behenyl alcohol, disodium EDTA, and palmitic acid. In some aspects, the composition includes: 0.1% to 3% w/w of triethanolamine, 0.1% to 3% w/w of dimethicone, 0.1% to 1.5% w/w of titanium dioxide, 0.1% to 1.5% w/w of betaine, 0.05% to 0.5% w/w of carbomer, 0.05% to 0.5% w/w of behenyl alcohol, 0.01% to 0.5% w/w of disodium EDTA, and 0.01% to 0.5% w/w of palmitic acid. In some aspects, the composition further includes *Opuntia tuna* fruit extract. In some aspects, the composition includes 0.0001% to 0.1% w/w of *Opuntia tuna* fruit extract. In some aspects, the composition is formulated as a mask.

In yet another aspect, disclosed is a foundation. In some aspects, the topical composition above further includes any one of, any combination of, or all of propanediol, caprylic/capric triglyceride, silica, cetearyl alcohol, *Butyrospermum parkii* (shea) butter, and glyceryl stearate. The amounts of the ingredients within the composition can vary (e.g., amounts can be as low as 0.000001% to as high as 98% w/w or any range therein). In some aspects, the composition includes: 5% to 20% w/w of propanediol, 5% to 15% w/w of caprylic/capric triglyceride, 1% to 10% w/w of silica, 0.5% to 5% w/w of cetearyl alcohol, 0.1% to 3% w/w of *Butyrospermum parkii* (shea) butter, and 0.1% to 3% w/w of glyceryl stearate. In some aspects, the composition further includes: PEG-100 stearate, hydroxyethyl acrylate/sodium acryloyldimethyl taurate copolymer, bis-diglyceryl polyacyladipate-2, squalene, isohexadecane, caprylyl glycol, chlorphenesin, tocopherol, dipotassium glycyrrhizate, and polysorbate 60. In some aspects, the composition includes: 0.1% to 3% w/w of PEG-100 stearate, 0.1% to 3% w/w of hydroxyethyl acrylate/sodium acryloyldimethyl taurate copolymer, 0.1% to 1.5% w/w of bis-diglyceryl polyacyladipate-2, 0.1% to 1.5% w/w of squalene, 0.1% to 1% w/w of isohexadecane, 0.1% to 1% w/w of caprylyl glycol, 0.05% to 0.5% w/w of chlorphenesin, 0.01% to 0.5% w/w of tocopherol, 0.01% to 0.5% w/w of dipotassium glycyrrhizate, and 0.01% to 0.5% w/w of polysorbate 60. In some aspects, the composition further includes a sunscreen agent. In some aspects, the composition includes octinoxate, homosalate, and oxybenzone. In some aspects, the composition includes 5% to 15% w/w of octinoxate, 1% to 10% w/w of homosalate, and 0.5% to 5% w/w of oxybenzone. In some aspects, the composition further includes *Opuntia tuna* fruit extract. In some aspects, the composition includes 0.0001% to 0.1% w/w of *Opuntia tuna* fruit extract. In some aspects, the composition is formulated as a foundation.

In yet another aspect, disclosed is a freshener. In some aspects, the topical composition above further includes any one of, any combination of, or all of PEG-40 hydrogenated castor oil, chlorphenesin, carbomer, polysorbate 20, triethanolamine, and hydrolyzed jojoba esters. The amounts of the ingredients within the composition can vary (e.g., amounts can be as low as 0.000001% to as high as 98% w/w or any range therein). In some aspects, the composition includes: 0.1% to 1% w/w of PEG-40 hydrogenated castor oil, 0.05% to 0.5% w/w of chlorphenesin, 0.05% to 0.5% w/w of carbomer, 0.05% to 0.5% w/w of polysorbate 20, 0.01% to 0.05% w/w of triethanolamine, and 0.01% to 0.05% w/w of hydrolyzed jojoba esters. In some aspects, the composition further includes *Opuntia tuna* fruit extract. In some aspects, the composition includes 0.0001% to 0.1% w/w of *Opuntia tuna* fruit extract. In some aspects, the composition is formulated as a freshener.

In some embodiments, disclosed is a cleanser. In some aspects, the topical composition above further includes any one of, any combination of, or all of petrolatum, PEG-6 caprylic/capric glycerides, glyceryl stearate, *Butyrosper-*

*mum parkii* (shea) butter, cetyl alcohol, and stearyl alcohol. The amounts of the ingredients within the composition can vary (e.g., amounts can be as low as 0.000001% to as high as 98% w/w or any range therein). In some aspects, the composition includes: 1% to 15% w/w of petrolatum, 1% to 10% w/w of PEG-6 caprylic/capric glycerides, 1% to 10% w/w of glyceryl stearate, 1% to 10% w/w of *Butyrospermum parkii* (shea) butter, 0.5% to 5% w/w of cetyl alcohol, and 0.1% to 3% w/w of stearyl alcohol. In some aspects, the composition further includes propylene glycol, cetearyl alcohol, triethanolamine, pentaerythrityl tetraisostearate, betaine, ceteth-20 phosphate, methylparaben, hydroxypropyl methylcellulose, dicetyl phosphate, dimethicone, butylated hydroxytoluene (BHT), carbomer, hydroxypropyl cyclodextrin, disodium EDTA, and dipotassium glycyrrhizate. In some aspects, the composition includes 0.1% to 3% w/w of propylene glycol, 0.1% to 3% w/w of cetearyl alcohol, 0.1% to 1.5% w/w of triethanolamine, 0.1% to 1.5% w/w of pentaerythrityl tetraisostearate, 0.1% to 1.5% w/w of betaine, 0.1% to 1% w/w of ceteth-20 phosphate, 0.05% to 1% w/w of methylparaben, 0.1% to 1% w/w of hydroxypropyl methylcellulose, 0.05% to 0.5% w/w of dicetyl phosphate, 0.05% to 0.5% w/w of dimethicone, 0.05% to 0.5% w/w of BHT, 0.01% to 0.5% w/w of carbomer, 0.01% to 0.5% w/w of hydroxypropyl cyclodextrin, 0.01% to 0.5% w/w of disodium EDTA, and 0.01% to 0.5% w/w of dipotassium glycyrrhizate. In some aspects, the composition further includes caprylyl glycol and decylene glycol. In some aspects, the composition includes 0.05% to 0.5% w/w of caprylyl glycol and 0.01% to 0.5% w/w of decylene glycol. In some aspects, the composition further includes *Opuntia tuna* fruit extract. In some aspects, the composition includes 0.0001% to 0.1% w/w of *Opuntia tuna* fruit extract. In some aspects, the composition is formulated as a cleanser.

The compositions disclosed herein may further comprise one or more ingredients described herein. For example, the composition may comprise one or more additional ingredients selected from one or more conditioning agents, moisturizing agents, pH adjusters, structuring agents, inorganic salts, and preservatives.

Methods of use for the compositions disclosed herein are also disclosed. In some aspects, the compositions disclosed are applied to skin and/or hair by applying the composition to skin and/or hair and leaving the composition on the skin and/or hair. In some aspects, the compositions disclosed are applied to skin and/or hair by applying the composition to skin and/or hair and removing the composition from the skin and/or hair. In some aspects, the compositions disclosed are removed immediately after applying the composition to up to 16 hours after applying the composition. In some embodiments, the compositions disclosed are used to moisturize skin and/or hair by applying the composition to skin and/or hair. In another aspect, the compositions disclosed are used to remove residue from skin and/or hair by applying the composition to skin and/or hair and removing the composition from the skin and/or hair. In yet another aspect, the compositions disclosed are used to cleanse skin and/or hair by applying the composition to skin and/or hair and removing the composition from the skin and/or hair.

Methods of use for the compositions disclosed herein are disclosed wherein in some embodiments, the compositions disclosed increase filaggrin production by applying the composition to skin, wherein filaggrin production is increased. In another aspect, the compositions disclosed moisturize the skin by applying the composition to skin, wherein skin moisture is increased. In yet another aspect, the compositions disclosed increase production of occludin by applying the composition to skin, wherein occludin production is increased. In some embodiments, the compositions disclosed inhibit production of TNFα by applying the composition to skin, wherein TNFα production is inhibited. In another aspect, the compositions disclosed prevents oxidative damage by applying the composition to skin and/or hair, wherein oxidative damage is prevented. In yet another aspect, the compositions disclosed decrease skin permeability by applying the composition to skin, wherein skin permeability is decreased. In some embodiments, the compositions disclosed are used to treat a subject in need thereof by applying the composition to skin, wherein skin permeability is decreased and wherein at least one of filaggrin production is increased, skin moisture is increased, occludin production is increased, TNFα production is inhibited, and/or oxidative damage is prevented.

In particular aspects, the compositions of the present invention are formulated as a topical skin composition. The composition can have a dermatologically acceptable vehicle or carrier for the compounds, compositions and extracts. The composition can further include a moisturizing agent or a humectant, a surfactant, a silicone containing compounds, a UV agent, an oil, and/or other ingredients identified in this specification or those known in the art. The composition can be a lotion, cream, gel, serum, emulsion (e.g., oil-in-water, water-in-oil, silicone-in-water, water-in-silicone, water-in-oil-in-water, oil-in-water-in-oil, oil-in-water-in-silicone, etc.), solutions (e.g., aqueous or hydro-alcoholic solutions), anhydrous bases (e.g., lipstick or a powder), ointments, milk, paste, aerosol, solid forms, eye jellies, etc. The composition can be in powdered form (e.g., dried, lyophilized, particulate, etc.). The composition can be formulated for topical skin application at least 1, 2, 3, 4, 5, 6, 7, or more times a day during use. In other aspects of the present invention, compositions can be storage stable or color stable, or both. It is also contemplated that the viscosity of the composition can be selected to achieve a desired result, e.g., depending on the type of composition desired, the viscosity of such composition can be from about 1 cps to well over 1 million cps or any range or integer derivable therein (e.g., 2 cps, 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, 200000, 300000, 400000, 500000, 600000, 700000, 800000, 900000, 1000000, 2000000, 3000000, 4000000, 5000000, 10000000, cps, etc., as measured on a Brookfield Viscometer using a TC spindle at 2.5 rpm at 25° C.).

The compositions of the present invention can also be modified to have a desired oxygen radical absorbance capacity (ORAC) value. In certain non-limiting aspects, the compositions of the present invention or the component or extracts thereof identified throughout this specification can be modified to have an ORAC value per mg of at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 70, 80, 90, 95, 100, 200, 300, 400, 500, 600, 700, 800, 900, 1000, 2000, 3000, 4000, 5000, 6000, 7000, 8000, 9000, 10000, 15000, 20000, 30000, 50000, 100000 or more or any range derivable therein.

The compositions in non-limiting aspects can have a pH of about 6 to about 9. In other aspects, the pH can be 1, 2, 3, 4, 5, 6, 7, 8, 9, 10, 11, 12, 13, or 14. The compositions can include a triglyceride. Non-limiting examples include small, medium, and large chain triglycerides. In certain aspects, the triglyceride is a medium chain triglyceride (e.g., caprylic capric triglyceride). The compositions can also include preservatives. Non-limiting examples of preservatives include methylparaben, propylparaben, or a mixture of methylparaben and propylparaben.

Compositions of the present invention can have UVA and UVB absorption properties. The compositions can have an sun protection factor (SPF) of 2, 3, 4, 5, 6, 7, 8, 9, 10, 11, 12, 13, 14, 15, 20, 25, 30, 35, 40, 45, 50, 55, 60, or more, or any integer or derivative therein. The compositions can be sunscreen lotions, sprays, or creams.

The compositions of the present invention can also include any one of, any combination of, or all of the following additional ingredients: water, a chelating agent, a moisturizing agent, a preservative, a thickening agent, a silicone containing compound, an essential oil, a structuring agent, a vitamin, a pharmaceutical ingredient, or an antioxidant, or any combination of such ingredients or mixtures of such ingredients. In certain aspects, the composition can include at least two, three, four, five, six, seven, eight, nine, ten, or all of these additional ingredients identified in the previous sentence. Non-limiting examples of these additional ingredients are identified throughout this specification and are incorporated into this section by reference. The amounts of such ingredients can range from 0.0001% to 99.9% by weight or volume of the composition, or any integer or range in between as disclosed in other sections of this specification, which are incorporated into this paragraph by reference.

Kits that include the compositions of the present invention are also contemplated. In certain embodiments, the composition is comprised in a container. The container can be a bottle, dispenser, or package. The container can dispense a pre-determined amount of the composition. In certain aspects, the compositions is dispensed in a spray, mist, dollop, or liquid. The container can include indicia on its surface. The indicia can be a word, an abbreviation, a picture, or a symbol.

It is also contemplated that the compositions disclosed throughout this specification can be used as a leave-on or rinse-off composition. By way of example, a leave-on composition can be one that is topically applied to skin and remains on the skin for a period of time (e.g., at least 5, 6, 7, 8, 9, 10, 20, or 30 minutes, or at least 1, 2, 3, 4, 5, 6, 7, 8, 9, 10, 11, 12, 13, 14, 15, 16, 17, 18, 19, 20, 21, 22, 23 or 24 hours, or overnight or throughout the day). Alternatively, a rinse-off composition can be a product that is intended to be applied to the skin and then removed or rinsed from the skin (e.g., with water) within a period of time such as less than 5, 4, 3, 2, or 1 minute. An example of a rinse of composition can be a skin cleanser, shampoo, conditioner, freshener, or soap. An example of a leave-on composition can be a skin moisturizer, sunscreen, mask, overnight cream, or a day cream.

It is contemplated that any embodiment discussed in this specification can be implemented with respect to any method or composition of the invention, and vice versa. Furthermore, compositions of the invention can be used to achieve methods of the invention.

In some embodiments, compositions of the present invention can be pharmaceutically or cosmetically elegant or can have pleasant tactile properties. "Pharmaceutically elegant," "cosmetically elegant," and/or "pleasant tactile properties" describes a composition that has particular tactile properties which feel pleasant on the skin (e.g., compositions that are not too watery or greasy, compositions that have a silky texture, compositions that are non-tacky or sticky, etc.). Pharmaceutically or cosmetically elegant can also relate to the creaminess or lubricity properties of the composition or to the moisture retaining properties of the composition.

Also contemplated is a product comprising a composition of the present invention. In non-limiting aspects, the product can be a cosmetic product. The cosmetic product can be those described in other sections of this specification or those known to a person of skill in the art. Non-limiting examples of products include a moisturizer, a cream, a lotion, a skin softener, a gel, a wash, a foundation, a night cream, a lipstick, a cleanser, a freshener, a toner, a sunscreen, a mask, an anti-aging product, a deodorant, an antiperspirant, a perfume, a cologne, etc.

Also disclosed are the following Embodiments 1 to 60 of the present invention. Embodiment 1 is a method of treating a subject in need thereof comprising applying a topical composition comprising hydrolyzed algae extract, saccharide isomerate, and a dermatologically acceptable vehicle to skin, wherein at least one of skin permeability is decreased, filaggrin production is increased, skin moisture is increased, occludin production is increased, TNFα production is inhibited, or oxidative damage is prevented. Embodiment 2 is the method of Embodiment 1, wherein skin permeability is decreased and wherein at least one of filaggrin production is increased, skin moisture is increased, occludin production is increased, TNFα production is inhibited, or oxidative damage is prevented. Embodiment 3 is the method of any of Embodiments 1 and 2, wherein the hydrolyzed algae extract increases production of filaggrin, increases skin moisture, increases production of occludin, and/or decreases skin permeability. Embodiment 4 is the method of any of Embodiments 1 to 3, wherein the saccharide isomerate increases production of filaggrin, increases skin moisture, increases production of occluding, inhibits TNFα production, and/or prevents oxidative damage. Embodiment 5 is the method of any of Embodiments 1 to 4, wherein the hydrolyzed algae extract comprises exopolysaccharides of *Halymenia durvillei*. Embodiment 6 is the method of any of Embodiments 1 to 5, wherein the saccharide isomerate comprises an exopolysaccharide synthesized by *Vibrio alginolyticus*. Embodiment 7 is the method of any of Embodiments 1 to 6, wherein the composition comprises 0.001% to 1% w/w of hydrolyzed algae extract and 0.0001% to 0.1% w/w of saccharide isomerate. Embodiment 8 is the method of any of Embodiments 1 to 7, wherein the composition is formulated as at least one of a moisturizer, a mask, a foundation, a freshener, and a cleanser. Embodiment 9 is the method of any of Embodiments 1 to 8, wherein the wherein the dermatologically acceptable vehicle comprises water. Embodiment 10 is the method of Embodiment 9, wherein the composition comprises 35% to 98% w/w of water. Embodiment 11 is the method of any of Embodiments 1 to 10, wherein the composition further comprises glycerin and phenoxyethanol. Embodiment 12 is the method of any of Embodiments 1 to 11, wherein the composition comprises 1% to 15% w/w of glycerin and 0.1% to 1.5% w/w of phenoxyethanol. Embodiment 13 is a topical composition comprising hydrolyzed algae extract, saccharide isomerate, and a dermatologically acceptable vehicle wherein the composition is capable of moisturizing at least one of skin and hair, wherein the saccharide isomerate comprises an exopolysaccharide synthesized by *Vibrio alginolyticus*, and the hydrolyzed algae extract comprises exopolysaccharides of *Halymenia durvillei*. Embodiment 14 is the composition of Embodiment 13, wherein the composition comprises an effective amount of saccharide isomerate capable of increasing production of filaggrin, increasing skin moisture, increasing production of occluding, inhibiting TNFα production, and/or preventing oxidative damage. Embodiment 15 is the composition of any of Embodiments 13 to 14, wherein the composition comprises an effective amount of hydrolyzed algae extract capable of increasing production of filaggrin, increasing skin moisture, increasing production of occludin, and/or decreasing skin permeability. Embodiment 16 is the composition of any of Embodiments 13 to 15, wherein the composition is capable of moisturizing at least one of dry skin and dry hair. Embodiment 17 is the composition of any of Embodiments 13 to 16, wherein the composition comprises 0.001% to 1% w/w of hydrolyzed algae extract and 0.0001% to 0.1% w/w of saccharide isomerate. Embodiment 18 is the composition of any of Embodiments 13 to 17, wherein the composition is formulated as at least one of a moisturizer, a mask, a foundation, a freshener, and a cleanser. Embodiment 19 is the composition of any of Embodiments 13 to 18, wherein the dermatologically acceptable vehicle comprises water. Embodiment 20 is the composition of any of Embodiments 13 to 19, wherein the composition comprises 35% to 98% w/w of water. Embodiment 21 is the composition of any of Embodiments 13 to 20, further comprising glycerin and phenoxyethanol. Embodiment 22 is the composition of any of Embodiments 13 to 21, wherein the composition comprises 1% to 15% w/w of glycerin and 0.1% to 1.5% w/w of phenoxyethanol. Embodiment 23 is the composition of any of Embodiments 13 to 22, wherein the composition further comprises: cyclopentasiloxane; hydrogenated polyisobutene; butylene glycol; dimethicone; octyldodecyl myristate; arachidyl alcohol; glyceryl stearate; cetearyl alcohol; petrolatum; and PEG-100 stearate. Embodiment 24 is the composition of Embodiment 23, wherein the composition comprises: 1% to 10% w/w of cyclopentasiloxane; 1% to 10% w/w of hydrogenated polyisobutene; 1% to 10% w/w of butylene glycol; 1% to 10% w/w of dimethicone; 0.5% to 5% w/w of octyldodecyl myristate; 0.5% to 5% w/w of arachidyl alcohol; 0.5% to 5% w/w of glyceryl stearate; 0.1% to 3% w/w of cetearyl alcohol; 0.1% to 3% w/w of petrolatum; and 0.1% to 3% w/w of PEG-100 stearate. Embodiment 25 is the composition of any of Embodiments 23 to 24, wherein the composition further comprises: behenyl alcohol; ammonium acryloyldimethyltaurate/VP copolymer; arachidyl glucoside; dimethicone/vinyl dimethicone crosspolymer; chlorphenesin; and disodium EDTA. Embodiment 26 is the composition of Embodiment 25, wherein the composition comprises: 0.1% to 3% w/w of behenyl alcohol; 0.1% to 1.5% w/w of ammonium acryloyldimethyltaurate/VP copolymer; 0.1% to 1.5% w/w of arachidyl glucoside; 0.1% to 1% w/w of dimethicone/vinyl dimethicone crosspolymer; 0.05% to 0.5% w/w of chlorphenesin; and 0.01% to 0.5% w/w of disodium EDTA. Embodiment 27 is the composition of any of Embodiments 23 to 26, wherein the composition further comprises *Opuntia tuna* fruit extract. Embodiment 28 is the composition of Embodiment 27, wherein the composition comprises 0.0001% to 0.1% w/w of *Opuntia tuna* fruit extract. Embodiment 29 is the composition of any of Embodiments 23 to 28, wherein the composition is formulated as a moisturizer. Embodiment 30 is the composition of any of Embodiments 13 to 22, wherein the composition further comprises: glyceryl stearate; petrolatum; stearic acid; cetyl alcohol; lauryl methacrylate/glycol dimethacrylate crosspolymer; and stearyl alcohol. Embodiment 31 is the composition of Embodiment 30, wherein the composition comprises: 1% to 10% w/w of glyceryl stearate; 1% to 10% w/w of petrolatum; 0.5% to 5% w/w of stearic acid; 0.5% to 5% w/w of cetyl alcohol; 0.1% to 3% w/w of lauryl methacrylate/glycol dimethacrylate crosspolymer; and 0.1% to 3% w/w of stearyl alcohol. Embodiment 32 is the composition of any of Embodiments 30 to 31, wherein the composition further comprises: triethanolamine; dimethicone; titanium dioxide; betaine; carbomer; behenyl alcohol; disodium EDTA; and palmitic acid. Embodiment 33 is the composition of Embodiment 32, wherein the composition comprises: 0.1% to 3% w/w of triethanolamine; 0.1% to 3% w/w of dimethicone; 0.1% to 1.5% w/w of titanium dioxide; 0.1% to 1.5% w/w of betaine; 0.05% to 0.5% w/w of carbomer; 0.05% to 0.5% w/w of behenyl alcohol; 0.01% to 0.5% w/w of disodium EDTA; and 0.01% to 0.5% w/w of palmitic acid. Embodiment 34 is the composition of any of Embodiments 30 to 33, wherein the composition further comprises *Opuntia tuna* fruit extract. Embodiment 35 is the composition of Embodiment 34, wherein the composition comprises 0.0001% to 0.1% w/w of *Opuntia tuna* fruit extract. Embodiment 36 is the composition of any of Embodiments 30 to 35, wherein the composition is formulated as a mask. Embodiment 37 is the composition of any of Embodiments 13 to 22, wherein the composition further comprises: propanediol; caprylic/capric triglyceride; silica; cetearyl alcohol; *Butyrospermum parkii* (shea) butter; and glyceryl stearate. Embodiment 38 is the composition of Embodiment 37, wherein the composition comprises: 5% to 20% w/w of propanediol; 5% to 15% w/w of caprylic/capric triglyceride; 1% to 10% w/w of silica; 0.5% to 5% w/w of cetearyl alcohol; 0.1% to 3% w/w of *Butyrospermum parkii* (shea) butter; and 0.1% to 3% w/w of glyceryl stearate. Embodiment 39 is the composition of any of Embodiments 37 to 38, wherein the composition further comprises: PEG-100 stearate; hydroxyethyl acrylate/sodium acryloyldimethyl taurate copolymer; bis-diglyceryl polyacyladipate-2; squalene; isohexadecane; caprylyl glycol; chlorphenesin; tocopherol; dipotassium glycyrrhizate; and polysorbate 60. Embodiment 40 is the composition of Embodiment 39, wherein the composition comprises: 0.1% to 3% w/w of PEG-100 stearate; 0.1% to 3% w/w of hydroxyethyl acrylate/sodium acryloyldimethyl taurate copolymer; 0.1% to 1.5% w/w of bis-diglyceryl polyacyladipate-2; 0.1% to 1.5% w/w of squalene; 0.1% to 1% w/w of isohexadecane; 0.1% to 1% w/w of caprylyl glycol; 0.05% to 0.5% w/w of chlorphenesin; 0.01% to 0.5% w/w of tocopherol; 0.01% to 0.5% w/w of dipotassium glycyrrhizate; and 0.01% to 0.5% w/w of polysorbate 60. Embodiment 41 is the composition of any of Embodiments 37 to 40, wherein the composition further comprises a sunscreen agent. Embodiment 42 is the composition of any of Embodiments 37 to 41, wherein the composition comprises: octinoxate; homosalate; and oxybenzone. Embodiment 43 is the composition of Embodiment 42, wherein the composition comprises: 5% to 15% w/w of octinoxate; 1% to 10% w/w of homosalate; and 0.5% to 5% w/w of oxybenzone. Embodiment 44 is the composition of any of Embodiments 37 to 43, wherein the composition further comprises *Opuntia tuna* fruit extract. Embodiment 45 is the composition of Embodiment 44, wherein the composition comprises 0.0001% to 0.1% w/w of *Opuntia tuna* fruit extract. Embodiment 46 is the composition of any of Embodiments 37 to 45, wherein the composition is formulated as a foundation. Embodiment 47 is the composition of any of Embodiments 13 to 22, wherein the composition further comprises: PEG-40 hydrogenated castor oil; chlorphenesin; carbomer; polysorbate 20; triethanolamine; and hydrolyzed jojoba esters. Embodiment 48 is the composition of Embodiment 47, wherein the composition comprises: 0.1% to 1% w/w of PEG-40 hydrogenated castor oil; 0.05% to 0.5% w/w of chlorphenesin; 0.05% to 0.5% w/w of carbomer; 0.05% to 0.5% w/w of polysorbate 20; 0.01% to 0.05% w/w of triethanolamine; and 0.01% to 0.05% w/w of hydrolyzed jojoba esters. Embodiment 49 is the composition of any of Embodiments 47 to 48, wherein the composition further comprises *Opuntia tuna* fruit extract. Embodiment 50 is the composition of Embodiment 49, wherein the composition comprises 0.0001% to 0.1% w/w of *Opuntia tuna* fruit extract. Embodiment 51 is the composition of any of Embodiments 47 to 50, wherein the composition is formulated as a freshener. Embodiment 52 is the composition of any of Embodiments 13 to 22, wherein the composition further comprises: petrolatum; PEG-6 caprylic/capric glycerides; glyceryl stearate; *Butyrospermum parkii* (shea) butter; cetyl alcohol; and stearyl alcohol. Embodiment 53 is the composition of Embodiment 52, wherein the composition comprises: 1% to 15% w/w of petrolatum; 1% to 10% w/w of PEG-6 caprylic/capric glycerides; 1% to 10% w/w of glyceryl stearate; 1% to 10% w/w of *Butyrospermum parkii* (shea) butter; 0.5% to 5% w/w of cetyl alcohol; and 0.1% to 3% w/w of stearyl alcohol. Embodiment 54 is the composition of any of Embodiments 52 to 53, wherein the composition further comprises: propylene glycol; cetearyl alcohol; triethanolamine; pentaerythrityl tetraisostearate; betaine; ceteth-20 phosphate; methylparaben; hydroxypropyl methylcellulose; dicetyl phosphate; dimethicone; BHT; carbomer; hydroxypropyl cyclodextrin; disodium EDTA; and dipotassium glycyrrhizate. Embodiment 55 is the composition of Embodiment 54, wherein the composition comprises: 0.1% to 3% w/w of propylene glycol; 0.1% to 3% w/w of cetearyl alcohol; 0.1% to 1.5% w/w of triethanolamine; 0.1% to 1.5% w/w of pentaerythrityl tetraisostearate; 0.1% to 1.5% w/w of betaine; 0.1% to 1% w/w of ceteth-20 phosphate; 0.05% to 1% w/w of methylparaben; 0.1% to 1% w/w of hydroxypropyl methylcellulose; 0.05% to 0.5% w/w of dicetyl phosphate; 0.05% to 0.5% w/w of dimethicone; 0.05% to 0.5% w/w of BHT; 0.01% to 0.5% w/w of carbomer; 0.01% to 0.5% w/w of hydroxypropyl cyclodextrin; 0.01% to 0.5% w/w of disodium EDTA; and 0.01% to 0.5% w/w of dipotassium glycyrrhizate. Embodiment 56 is the composition of any of Embodiments 52 to 55, wherein the composition further comprises caprylyl glycol and decylene glycol. Embodiment 57 is the composition of Embodiment 56, wherein the composition comprises 0.05% to 0.5% w/w of caprylyl glycol and 0.01% to 0.5% w/w of decylene glycol. Embodiment 58 is the composition of any of Embodiments 52 to 57, wherein the composition further comprises *Opuntia tuna* fruit extract. Embodiment 59 is the composition of Embodiment 58, wherein the composition comprises 0.0001% to 0.1% w/w of *Opuntia tuna* fruit extract. Embodiment 60 is the composition of any of Embodiments 52 to 59, wherein the composition is formulated as a cleanser.

"Topical application" means to apply or spread a composition onto the surface of lips or keratinous tissue. "Topical skin composition" includes compositions suitable for topical application on lips or keratinous tissue. Such compositions are typically dermatologically-acceptable in that they do not have undue toxicity, incompatibility, instability, allergic response, and the like, when applied to lips or skin. Topical skin care compositions of the present invention can have a selected viscosity to avoid significant dripping or pooling after application to skin.

"Keratinous tissue" includes keratin-containing layers disposed as the outermost protective covering of mammals and includes, but is not limited to, lips, skin, hair and nails.

The term "about" or "approximately" are defined as being close to as understood by one of ordinary skill in the art, and in one non-limiting embodiment the terms are defined to be within 10%, preferably within 5%, more preferably within 1%, and most preferably within 0.5%.

The term "substantially" and its variations are defined as being largely but not necessarily wholly what is specified as understood by one of ordinary skill in the art, and in one non-limiting embodiment substantially refers to ranges within 10%, within 5%, within 1%, or within 0.5%.

The terms "inhibiting" or "reducing" or any variation of these terms includes any measurable decrease or complete inhibition to achieve a desired result. The terms "promote" or "increase" or any variation of these terms includes any measurable increase or production of a protein or molecule (e.g., matrix proteins such as fibronectin, laminin, collagen, or elastin or molecules such as hyaluronic acid) to achieve a desired result.

"Treating" or any variation of this term includes any measurable improvement in a disease, condition, or symptom that is being treated or is associated with the disease, condition, or symptom being treated.

"Preventing" or any variation of this term means to slow, stop, or reverse progression toward a result. The prevention may be any slowing of the progression toward the result.

The term "effective," as that term is used in the specification and/or claims, means adequate to accomplish a desired, expected, or intended result.

The use of the word "a" or "an" when used in conjunction with the term "comprising" in the claims and/or the specification may mean "one," but it is also consistent with the meaning of "one or more," "at least one," and "one or more than one."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The compositions and methods for their use can "comprise," "consist essentially of," or "consist of" any of the ingredients or steps disclosed throughout the specification.

Other objects, features and advantages of the present invention will become apparent from the following detailed description. It should be understood, however, that the detailed description and the examples, while indicating specific embodiments of the invention, are given by way of illustration only. Additionally, it is contemplated that changes and modifications within the spirit and scope of the invention will become apparent to those skilled in the art from this detailed description.

DESCRIPTION OF ILLUSTRATIVE EMBODIMENTS

As noted above, several of the unique aspects of the present invention are the combination of hydrolyzed algae extract and saccharide isomerate in a topical composition and the use of such compositions to moisturize and/or improve the appearance and/or condition of skin and/or hair, decrease skin permeability, increase filaggrin production, increase skin moisture, increase occludin production, inhibit TNFα production, and/or prevent oxidative damage. This allows for the benefits of stable topical compositions with the benefits outlined.

Some embodiments are designed to work as a moisturizer. An example of such a composition is provided in Example 1, Table 1. Some embodiments are designed to work as a mask. An example of such a composition is provided in Example 1, Table 2. Some embodiments are designed to work as a foundation. An example of such a composition is provided in Example 1, Table 3. Some embodiments are designed to work as a freshener. An example of such a composition is provided in Example 1, Table 4. Some embodiments are designed to work as a cleanser. An example of such a composition is provided in Example 1, Tables 5 and 6.

These and other non-limiting aspects of the present invention are provided in the following subsections.

A. DETERMINING SKIN-TYPE

The compositions of the present invention utilize unique combinations of ingredients, which can be used to create a formulation for a particular skin type (e.g., normal, dry, oily, or combination skin). The compositions of the present invention, however, can be used across all skin types while reducing any skin irritating effects. For instance, the unique combination of ingredients disclosed herein can be used for, but is not limited to use for, dry skin and/or hair.

The following are non-limiting examples of how skin type may be determined. There are also other well-known methods for determining a person's skin type. There are three main skin types: (1) normal skin; (2) dry skin; and (3) oily skin. A fourth skin type is simply a combination of any one of normal, dry, or oily skin (e.g., normal/dry, normal/oily, oily/dry).

Normal skin, for instance, can be identified as having a smooth texture and no greasy patches or flaky areas. Therefore, a product that can retain skin moisture in its present form can be used to maintain the appearance of normal skin.

As for dry skin, it has a low level of sebum production from sebaceous glands and is prone to irritation or erythema. The appearance of dry skin has a parched look caused by the skin's inability to retain moisture. Oftentimes it feels "tight" and uncomfortable after washing and is prone to chapping, flaking, and cracking. Dry skin can be exacerbated by wind, extremes of temperature and air-conditioning, all of which cause the skin to flake, chap and feel tight. Dry skin typically has a dull appearance. Therefore, a product that deliver appropriate hydration and restore moisture to dry skin can be used to counteract the effects of dry skin.

With respect to oily skin, such skin is shiny, thick and dull colored. It feels oily and has coarse pores and pimples and other unsightly blemishes due to overproduction of sebum from sebaceous glands and from clogged/blocked pores. In this regard, oily skin usually has oil producing sebaceous glands that are overactive and produce more oil than is needed. The oil oozes and gives the skin a greasy shine. The pores are enlarged and the skin has a coarse look. Therefore, a product that can help control skin surface oiliness while also retaining appropriate skin moisture can be used to counteract the effects of oily skin.

As noted above, combination skin is a combination of both oily, dry, and/or normal skin (e.g., normal/dry, oily/dry, normal/oily). For oily/dry skin, there is typically a greasy center panel consisting of nose, forehead and chin (also known as the "T-zone" of a person's face) and a dry panel consisting of cheeks, mouth and the areas around the eyes. Therefore, a product that can control the excess oil production in sebaceous glands in the T-zone while also hydrating the dry skin areas outside of the T-zone can be used for such oily/dry skin.

Once a particular skin-type is identified, a person can then select an appropriate composition to correct or maintain the skin-type.

B. COMBINATION OF INGREDIENTS

It has been found that a combination of ingredients—hydrolyzed algae extract and saccharide isomerate—can be used to moisturize and/or improve the appearance and/or condition of skin and/or hair. These ingredients are discussed in more detail below.

Hydrolyzed algae extract contains exopolysaccharides of *Halymenia durvillei*. In some embodiments this ingredient is an aqueous extraction. In some embodiments this ingredient is commercially available, e.g., from Greentech Biotechnologies, which provides hydrolyzed algae extract under the trade name Xcell-30® SN. It has been determined that this ingredient can be used to increases production of filaggrin, increases skin moisture, increases production of occludin, and decreases skin permeability.

Saccharide isomerate is an exopolysaccharide synthesized by a micro-organism called *Vibrio alginolyticus* and belonging to the family of *Thalasso* plankton. In some embodiments this ingredient is commercially available, e.g., from Barnet, which provides saccharide isomerate under the trade name Benoiderm. It has been determined that this ingredient can be used to increase production of filaggrin, increase skin moisture, increase production of occludin, inhibit TNFα production, and prevent oxidative damage.

The extracts described herein can be extracts made through extraction methods known in the art and combinations thereof. Non-limiting examples of extraction methods include the use of liquid-liquid extraction, solid phase extraction, aqueous extraction, ethyl acetate, alcohol, acetone, oil, supercritical carbon dioxide, heat, pressure, pressure drop extraction, ultrasonic extraction, etc. Extracts can be a liquid, solid, dried liquid, re-suspended solid, etc.

C. AMOUNTS OF INGREDIENTS

It is contemplated that the compositions of the present invention can include any amount of the ingredients discussed in this specification. The compositions can also include any number of combinations of additional ingredients described throughout this specification (e.g., pigments, or additional cosmetic or pharmaceutical ingredients). The concentrations of the any ingredient within the compositions can vary. In non-limiting embodiments, for example, the compositions can comprise, consisting essentially of, or consist of, in their final form, for example, at least about 0.0001%, 0.0002%, 0.0003%, 0.0004%, 0.0005%, 0.0006%, 0.0007%, 0.0008%, 0.0009%, 0.0010%, 0.0011%, 0.0012%, 0.0013%, 0.0014%, 0.0015%, 0.0016%, 0.0017%, 0.0018%, 0.0019%, 0.0020%, 0.0021%, 0.0022%, 0.0023%, 0.0024%, 0.0025%, 0.0026%, 0.0027%, 0.0028%, 0.0029%, 0.0030%, 0.0031%, 0.0032%, 0.0033%, 0.0034%, 0.0035%, 0.0036%, 0.0037%, 0.0038%, 0.0039%, 0.0040%, 0.0041%, 0.0042%, 0.0043%, 0.0044%, 0.0045%, 0.0046%, 0.0047%, 0.0048%, 0.0049%, 0.0050%, 0.0051%, 0.0052%, 0.0053%, 0.0054%, 0.0055%, 0.0056%, 0.0057%, 0.0058%, 0.0059%, 0.0060%, 0.0061%, 0.0062%, 0.0063%, 0.0064%, 0.0065%, 0.0066%, 0.0067%, 0.0068%, 0.0069%, 0.0070%, 0.0071%, 0.0072%, 0.0073%, 0.0074%, 0.0075%, 0.0076%, 0.0077%, 0.0078%, 0.0079%, 0.0080%, 0.0081%, 0.0082%, 0.0083%, 0.0084%, 0.0085%, 0.0086%, 0.0087%, 0.0088%, 0.0089%, 0.0090%, 0.0091%, 0.0092%, 0.0093%, 0.0094%, 0.0095%, 0.0096%, 0.0097%, 0.0098%, 0.0099%, 0.0100%, 0.0200%, 0.0250%, 0.0275%, 0.0300%, 0.0325%, 0.0350%, 0.0375%, 0.0400%, 0.0425%, 0.0450%, 0.0475%, 0.0500%, 0.0525%, 0.0550%, 0.0575%, 0.0600%, 0.0625%, 0.0650%, 0.0675%, 0.0700%, 0.0725%, 0.0750%, 0.0775%, 0.0800%, 0.0825%, 0.0850%, 0.0875%, 0.0900%, 0.0925%, 0.0950%, 0.0975%, 0.1000%, 0.1250%, 0.1500%, 0.1750%, 0.2000%, 0.2250%, 0.2500%, 0.2750%, 0.3000%, 0.3250%, 0.3500%, 0.3750%, 0.4000%, 0.4250%, 0.4500%, 0.4750%, 0.5000%, 0.5250%, 0.5550%, 0.5750%, 0.6000%, 0.6250%, 0.6500%, 0.6750%, 0.7000%, 0.7250%, 0.7500%, 0.7750%, 0.8000%, 0.8250%, 0.8500%, 0.8750%, 0.9000%, 0.9250%, 0.9500%, 0.9750%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9%, 5.0%, 5.1%, 5.2%, 5.3%, 5.4%, 5.5%, 5.6%, 5.7%, 5.8%, 5.9%, 6.0%, 6.1%, 6.2%, 6.3%, 6.4%, 6.5%, 6.6%, 6.7%, 6.8%, 6.9%, 7.0%, 7.1%, 7.2%, 7.3%, 7.4%, 7.5%, 7.6%, 7.7%, 7.8%, 7.9%, 8.0%, 8.1%, 8.2%, 8.3%, 8.4%, 8.5%, 8.6%, 8.7%, 8.8%, 8.9%, 9.0%, 9.1%, 9.2%, 9.3%, 9.4%, 9.5%, 9.6%, 9.7%, 9.8%, 9.9%, 10%, 11%, 12%, 13%, 14%, 15%, 16%, 17%, 18%, 19%, 20%, 21%, 22%, 23%, 24%, 25%, 26%, 27%, 28%, 29%, 30%, 35%, 40%, 45%, 50%, 60%, 65%, 70%, 75%, 80%, 85%, 90%, 95%, or 99% or any range derivable therein, of at least one of the ingredients that are mentioned throughout the specification and claims. In non-limiting aspects, the percentage can be calculated by weight or volume of the total composition. A person of ordinary skill in the art would understand that the concentrations can vary depending on the addition, substitution, and/or subtraction of ingredients in a given composition.

D. VEHICLES

The compositions of the present invention can include or be incorporated into all types of vehicles and carriers. The vehicle or carrier can be a pharmaceutically or dermatologically acceptable vehicle or carrier. Non-limiting examples of vehicles or carriers include water, glycerin, alcohol, oil, a silicon containing compound, a silicone compound, and wax. Variations and other appropriate vehicles will be apparent to the skilled artisan and are appropriate for use in the present invention. In certain aspects, the concentrations and combinations of the compounds, ingredients, and agents can be selected in such a way that the combinations are chemically compatible and do not form complexes which precipitate from the finished product.

E. STRUCTURE

The compositions of the present invention can be structured or formulated into a variety of different forms. Non-limiting examples include emulsions (e.g., water-in-oil, water-in-oil-in-water, oil-in-water, silicone-in-water, water-in-silicone, oil-in-water-in-oil, oil-in-water-in-silicone emulsions), creams, lotions, solutions (both aqueous and hydro-alcoholic), anhydrous bases (such as lipsticks and powders), gels, masks, peels, and ointments. Variations and other structures will be apparent to the skilled artisan and are appropriate for use in the present invention.

F. ADDITIONAL INGREDIENTS

In addition to the combination of ingredients disclosed by the inventors, the compositions can also include additional ingredients such as cosmetic ingredients and pharmaceutical active ingredients. Non-limiting examples of these additional ingredients are described in the following subsections.

1. Cosmetic Ingredients

The CTFA International Cosmetic Ingredient Dictionary and Handbook (2004 and 2008) describes a wide variety of non-limiting cosmetic ingredients that can be used in the context of the present invention. Examples of these ingredient classes include: fragrance agents (artificial and natural; e.g., gluconic acid, phenoxyethanol, and triethanolamine), dyes and color ingredients (e.g., Blue 1, Blue 1 Lake, Red 40, titanium dioxide, D&C blue no. 4, D&C green no. 5, D&C orange no. 4, D&C red no. 17, D&C red no. 33, D&C violet no. 2, D&C yellow no. 10, and D&C yellow no. 11), flavoring agents/aroma agents (e.g., *Stevia rebaudiana* (sweetleaf) extract, and menthol), adsorbents, lubricants, solvents, moisturizers (including, e.g., emollients, humectants, film formers, occlusive agents, and agents that affect the natural moisturization mechanisms of the skin), water-repellants, UV absorbers (physical and chemical absorbers such as para-aminobenzoic acid ("PABA") and corresponding PABA derivatives, titanium dioxide, zinc oxide, etc.), essential oils, vitamins (e.g., A, B, C, D, E, and K), trace metals (e.g., zinc, calcium and selenium), anti-irritants (e.g., steroids and non-steroidal anti-inflammatories), botanical extracts (e.g., *Aloe vera*, chamomile, cucumber extract, *Ginkgo biloba*, *ginseng*, and rosemary), anti-microbial agents, antioxidants (e.g., BHT and tocopherol), chelating agents (e.g., disodium EDTA and tetrasodium EDTA), preservatives (e.g., methylparaben and propylparaben), pH adjusters (e.g., sodium hydroxide and citric acid), absorbents (e.g., aluminum starch octenylsuccinate, kaolin, corn starch, oat starch, cyclodextrin, talc, and zeolite), skin bleaching and lightening agents (e.g., hydroquinone and niacinamide lactate), humectants (e.g., sorbitol, urea, methyl gluceth-20, plankton extract, and mannitol), exfoliants, waterproofing agents (e.g., magnesium/aluminum hydroxide stearate), skin conditioning agents (e.g., *aloe* extracts, allantoin, bisabolol, ceramides, dimethicone, hyaluronic acid, biosaccharide gum-1, ethylhexylglycerin, pentylene glycol, hydrogenated polydecene, octyldodecyl oleate, and dipotassium glycyrrhizate). Non-limiting examples of some of these ingredients are provided in the following subsections.

a. UV Absorption Agents

UV absorption agents that can be used in combination with the compositions of the present invention include chemical and physical sunblocks. Non-limiting examples of chemical sunblocks that can be used include para-aminobenzoic acid (PABA), PABA esters (glyceryl PABA, amyldimethyl PABA and octyldimethyl PABA), butyl PABA, ethyl PABA, ethyl dihydroxypropyl PABA, benzophenones (oxybenzone, sulisobenzone, benzophenone, and benzophenone-1 through 12), cinnamates (octyl methoxycinnamate, isoamyl p-methoxycinnamate, octylmethoxy cinnamate, cinoxate, diisopropyl methyl cinnamate, DEA-methoxycinnamate, ethyl diisopropylcinnamate, glyceryl octanoate dimethoxycinnamate and ethyl methoxycinnamate), cinnamate esters, salicylates (homomethyl salicylate, benzyl salicylate, glycol salicylate, isopropylbenzyl salicylate, etc.), anthranilates, ethyl urocanate, homosalate, octisalate, dibenzoylmethane derivatives (e.g., avobenzone), octocrylene, octyl triazone, digalloyl trioleate, glyceryl aminobenzoate, lawsone with dihydroxyacetone, ethylhexyl triazone, dioctyl butamido triazone, benzylidene malonate polysiloxane, terephthalylidene dicamphor sulfonic acid, disodium phenyl dibenzimidazole tetrasulfonate, diethylamino hydroxybenzoyl hexyl benzoate, bis diethylamino hydroxybenzoyl benzoate, bis benzoxazoylphenyl ethylhexylimino triazine, drometrizole trisiloxane, methylene bis-benzotriazolyl tetramethylbutylphenol, and bis-ethylhexyloxyphenol methoxyphenyltriazine, 4-methylbenzylidene camphor, and isopentyl 4-methoxycinnamate. Non-limiting examples of physical sunblocks include, kaolin, talc, petrolatum and metal oxides (e.g., titanium dioxide and zinc oxide).

b. Moisturizing Agents

Non-limiting examples of moisturizing agents that can be used with the compositions of the present invention include amino acids, chondroitin sulfate, diglycerin, erythritol, fructose, glucose, glycerin, glycerol polymers, glycol, 1,2,6-hexanetriol, honey, hyaluronic acid, hydrogenated honey, hydrogenated starch hydrolysate, inositol, lactitol, maltitol, maltose, mannitol, natural moisturizing factor, PEG-15 butanediol, plankton extract, polyglyceryl sorbitol, salts of pyrrolidone carboxylic acid, potassium PCA, propylene glycol, sodium glucuronate, sodium PCA, sorbitol, sucrose, trehalose, urea, and xylitol.

Other examples include acetylated lanolin, acetylated lanolin alcohol, alanine, algae extract, *Aloe barbadensis, Aloe barbadensis* extract, *Aloe barbadensis* gel, *Althea officinalis* extract, apricot (*Prunus armeniaca*) kernel oil, arginine, arginine aspartate, *Arnica montana* extract, aspartic acid, avocado (*Persea gratissima*) oil, barrier sphingolipids, butyl alcohol, beeswax, behenyl alcohol, beta-sitosterol, birch (*Betula alba*) bark extract, borage (*Borago officinalis*) extract, butcherbroom (*Ruscus aculeatus*) extract, butylene glycol, *Calendula officinalis* extract, *Calendula officinalis* oil, candelilla (*Euphorbia cerifera*) wax, canola oil, caprylic/capric triglyceride, cardamom (*Elettaria cardamomum*) oil, carnauba (*Copernicia cerifera*) wax, carrot (*Daucus carota sativa*) oil, castor (*Ricinus communis*) oil, ceramides, ceresin, ceteareth-5, ceteareth-12, ceteareth-20, cetearyl octanoate, ceteth-20, ceteth-24, cetyl acetate, cetyl octanoate, cetyl palmitate, chamomile (*Anthemis nobilis*) oil, cholesterol, cholesterol esters, cholesteryl hydroxystearate, citric acid, clary (*Salvia sclarea*) oil, cocoa (*Theobroma cacao*) butter, coco-caprylate/caprate, coconut (*Cocos nucifera*) oil, collagen, collagen amino acids, corn (*Zea mays*) oil, fatty acids, decyl oleate, dimethicone copolyol, dimethiconol, dioctyl adipate, dioctyl succinate, dipentaerythrityl hexacaprylate/hexacaprate, DNA, erythritol, ethoxydiglycol, ethyl linoleate, *Eucalyptus globulus* oil, evening primrose (*Oenothera biennis*) oil, fatty acids, *Geranium maculatum* oil, glucosamine, glucose glutamate, glutamic acid, glycereth-26, glycerin, glycerol, glyceryl distearate, glyceryl hydroxystearate, glyceryl laurate, glyceryl linoleate, glyceryl myristate, glyceryl oleate, glyceryl stearate, glyceryl stearate SE, glycine, glycol stearate, glycol stearate SE, glycosaminoglycans, grape (*Vitis vinifera*) seed oil, hazel (*Corylus americana*) nut oil, hazel (*Corylus avellana*) nut oil, hexylene glycol, hyaluronic acid, hybrid safflower (*Carthamus tinctorius*) oil, hydrogenated castor oil, hydrogenated coco-glycerides, hydrogenated coconut oil, hydrogenated lanolin, hydrogenated lecithin, hydrogenated palm glyceride, hydrogenated palm kernel oil, hydrogenated soybean oil, hydrogenated tallow glyceride, hydrogenated vegetable oil, hydrolyzed collagen, hydrolyzed elastin, hydrolyzed glycosaminoglycans, hydrolyzed keratin, hydrolyzed soy protein, hydroxylated lanolin, hydroxyproline, isocetyl stearate, isocetyl stearoyl stearate, isodecyl oleate, isopropyl isostearate, isopropyl lanolate, isopropyl myristate, isopropyl palmitate, isopropyl stearate, isostearamide DEA, isostearic acid, isostearyl lactate, isostearyl neopentanoate, jasmine (*Jasminum officinale*) oil, jojoba (*Buxus chinensis*) oil, kelp, kukui (*Aleurites moluccana*) nut oil, lactamide MEA, laneth-16, laneth-10 acetate, lanolin, lanolin acid, lanolin alcohol, lanolin oil, lanolin wax, lavender (*Lavandula angustifolia*) oil, lecithin, lemon (*Citrus medica limonum*) oil, linoleic acid, linolenic acid, *Macadamia ternifolia* nut oil, maltitol, matricaria (*Chamomilla recutita*) oil, methyl glucose sesquistearate, methylsilanol PCA, mineral oil, mink oil, mortierella oil, myristyl lactate, myristyl myristate, myristyl propionate, neopentyl glycol dicaprylate/dicaprate, octyldodecanol, octyldodecyl myristate, octyldodecyl stearoyl stearate, octyl hydroxystearate, octyl palmitate, octyl salicylate, octyl stearate, oleic acid, olive (*Olea europaea*) oil, orange (*Citrus aurantium dulcis*) oil, palm (*Elaeis guineensis*) oil, palmitic acid, pantethine, panthenol, panthenyl ethyl ether, paraffin, PCA, peach (*Prunus persica*) kernel oil, peanut (*Arachis hypogaea*) oil, PEG-8 C12-18 ester, PEG-15 cocamine, PEG-150 distearate, PEG-60 glyceryl isostearate, PEG-5 glyceryl stearate, PEG-30 glyceryl stearate, PEG-7 hydrogenated castor oil, PEG-40 hydrogenated castor oil, PEG-60 hydrogenated castor oil, PEG-20 methyl glucose sesquistearate, PEG-40 sorbitan peroleate, PEG-5 soy sterol, PEG-10 soy sterol, PEG-2 stearate, PEG-8 stearate, PEG-20 stearate, PEG-32 stearate, PEG-40 stearate, PEG-50 stearate, PEG-100 stearate, PEG-150 stearate, pentadecalactone, peppermint (*Mentha piperita*) oil, petrolatum, phospholipids, plankton extract, polyamino sugar condensate, polyglyceryl-3 diisostearate, polyquaternium-24, polysorbate 20, polysorbate 40, polysorbate 60, polysorbate 80, polysorbate 85, potassium myristate, potassium palmitate, propylene glycol, propylene glycol dicaprylate/dicaprate, propylene glycol dioctanoate, propylene glycol dipelargonate, propylene glycol laurate, propylene glycol stearate, propylene glycol stearate SE, PVP, pyridoxine dipalmitate, retinol, retinyl palmitate, rice (*Oryza sativa*) bran oil, RNA, rosemary (*Rosmarinus officinalis*) oil, rose oil, safflower (*Carthamus tinctorius*) oil, sage (*Salvia officinalis*) oil, sandalwood (*Santalum album*) oil, serine, serum protein, sesame (*Sesamum indicum*) oil, shea butter (*Butyrospermum parkii*), silk powder, sodium chondroitin sulfate, sodium hyaluronate, sodium lactate, sodium palmitate, sodium PCA, sodium polyglutamate, soluble collagen, sorbitan laurate, sorbitan oleate, sorbitan palmitate, sorbitan sesquioleate, sorbitan stearate, sorbitol, soybean (*Glycine soja*) oil, sphingolipids, squalane, squalene, stearamide MEA-stearate, stearic acid, stearoxy dimethicone, stearoxytrimethylsilane, stearyl alcohol, stearyl glycyrrhetinate, stearyl heptanoate, stearyl stearate, sunflower (*Helianthus annuus*) seed oil, sweet almond (*Prunus amygdalus dulcis*) oil, synthetic beeswax, tocopherol, tocopheryl acetate, tocopheryl linoleate, tribehenin, tridecyl neopentanoate, tridecyl stearate, triethanolamine, tristearin, urea, vegetable oil, water, waxes, wheat (*Triticum vulgare*) germ oil, and ylang ylang (*Cananga odorata*) oil.

c. Antioxidants

Non-limiting examples of antioxidants that can be used with the compositions of the present invention include acetyl cysteine, ascorbic acid polypeptide, ascorbyl dipalmitate, ascorbyl methylsilanol pectinate, ascorbyl palmitate, ascorbyl stearate, BHA, BHT, t-butyl hydroquinone, cysteine, cysteine HCl, diamylhydroquinone, di-t-butylhydroquinone, dicetyl thiodipropionate, dioleyl tocopheryl methylsilanol, disodium ascorbyl sulfate, distearyl thiodipropionate, ditridecyl thiodipropionate, dodecyl gallate, erythorbic acid, esters of ascorbic acid, ethyl ferulate, ferulic acid, gallic acid esters, hydroquinone, isooctyl thioglycolate, kojic acid, magnesium ascorbate, magnesium ascorbyl phosphate, methylsilanol ascorbate, natural botanical anti-oxidants such as green tea or grape seed extracts, nordihydroguaiaretic acid, octyl gallate, phenylthioglycolic acid, potassium ascorbyl tocopheryl phosphate, potassium sulfite, propyl gallate, quinones, rosmarinic acid, sodium ascorbate, sodium bisulfite, sodium erythorbate, sodium metabisulfite, sodium sulfite, superoxide dismutase, sodium thioglycolate, sorbityl furfural, thiodiglycol, thiodiglycolamide, thiodiglycolic acid, thioglycolic acid, thiolactic acid, thiosalicylic acid, tocophereth-5, tocophereth-10, tocophereth-12, tocophereth-18, tocophereth-50, tocopherol, tocophersolan, tocopheryl acetate, tocopheryl linoleate, tocopheryl nicotinate, tocopheryl succinate, and tris(nonylphenyl)phosphite.

d. Structuring Agents

In other non-limiting aspects, the compositions of the present invention can include a structuring agent. Structuring agent, in certain aspects, assist in providing rheological characteristics to the composition to contribute to the composition's stability. In other aspects, structuring agents can also function as an emulsifier or surfactant. Non-limiting examples of structuring agents include stearic acid, palmitic acid, stearyl alcohol, cetyl alcohol, behenyl alcohol, stearic acid, the polyethylene glycol ether of stearyl alcohol having an average of about 1 to about 21 ethylene oxide units, the polyethylene glycol ether of cetyl alcohol having an average of about 1 to about 5 ethylene oxide units, and mixtures thereof.

e. Emulsifiers

In certain aspects of the present invention, the compositions do not include an emulsifier. In other aspects, however, the compositions can include one or more emulsifiers. Emulsifiers can reduce the interfacial tension between phases and improve the formulation and stability of an emulsion. The emulsifiers can be nonionic, cationic, anionic, and zwitterionic emulsifiers (See McCutcheon's (1986); U.S. Pat. Nos. 5,011,681; 4,421,769; 3,755,560). Non-limiting examples include esters of glycerin, esters of propylene glycol, fatty acid esters of polyethylene glycol, fatty acid esters of polypropylene glycol, esters of sorbitol, esters of sorbitan anhydrides, carboxylic acid copolymers, esters and ethers of glucose, ethoxylated ethers, ethoxylated alcohols, alkyl phosphates, polyoxyethylene fatty ether phosphates, fatty acid amides, acyl lactylates, soaps, TEA stearate, DEA oleth-3 phosphate, polyethylene glycol 20 sorbitan monolaurate (polysorbate 20), polyethylene glycol 5 soya sterol, steareth-2, steareth-20, steareth-21, ceteareth-20, cetearyl glucoside, cetearyl alcohol, C12-13 pareth-3, PPG-2 methyl glucose ether distearate, PPG-5-ceteth-20, bis-PEG/PPG-20/20 dimethicone, ceteth-10, polysorbate 80, cetyl phosphate, potassium cetyl phosphate, diethanolamine cetyl phosphate, polysorbate 60, glyceryl stearate, PEG-100 stearate, arachidyl alcohol, arachidyl glucoside, and mixtures thereof.

f. Silicone Containing Compounds

In non-limiting aspects, silicone containing compounds include any member of a family of polymeric products whose molecular backbone is made up of alternating silicon and oxygen atoms with side groups attached to the silicon atoms. By varying the —Si—O— chain lengths, side groups, and crosslinking, silicones can be synthesized into a wide variety of materials. They can vary in consistency from liquid to gel to solids.

The silicone containing compounds that can be used in the context of the present invention include those described in this specification or those known to a person of ordinary skill in the art. Non-limiting examples include silicone oils (e.g., volatile and non-volatile oils), gels, and solids. In certain aspects, the silicon containing compounds includes a silicone oils such as a polyorganosiloxane. Non-limiting examples of polyorganosiloxanes include dimethicone, cyclomethicone, polysilicone-11, phenyl trimethicone, trimethylsilylamodimethicone, stearoxytrimethylsilane, or mixtures of these and other organosiloxane materials in any given ratio in order to achieve the desired consistency and application characteristics depending upon the intended application (e.g., to a particular area such as the skin, hair, or eyes). A "volatile silicone oil" includes a silicone oil have a low heat of vaporization, i.e. normally less than about 50 cal per gram of silicone oil. Non-limiting examples of volatile silicone oils include: cyclomethicones such as Dow Corning 344 Fluid, Dow Corning 345 Fluid, Dow Corning 244 Fluid, and Dow Corning 245 Fluid, Volatile Silicon 7207 (Union Carbide Corp., Danbury, Conn.); low viscosity dimethicones, i.e. dimethicones having a viscosity of about 50 cst or less (e.g., dimethicones such as Dow Corning 200-0.5 cst Fluid). The Dow Corning Fluids are available from Dow Corning Corporation, Midland, Mich. Cyclomethicone and dimethicone are described in the Third Edition of the CTFA Cosmetic Ingredient Dictionary (incorporated by reference) as cyclic dimethyl polysiloxane compounds and a mixture of fully methylated linear siloxane polymers end-blocked with trimethylsiloxy units, respectively. Other non-limiting volatile silicone oils that can be used in the context of the present invention include those available from General Electric Co., Silicone Products Div., Waterford, N.Y. and SWS Silicones Div. of Stauffer Chemical Co., Adrian, Mich.

g. Essential Oils

Essential oils include oils derived from herbs, flowers, trees, and other plants. Such oils are typically present as tiny droplets between the plant's cells, and can be extracted by several method known to those of skill in the art (e.g., steam distilled, enfleurage (i.e., extraction by using fat), maceration, solvent extraction, or mechanical pressing). When these types of oils are exposed to air they tend to evaporate (i.e., a volatile oil). As a result, many essential oils are colorless, but with age they can oxidize and become darker. Essential oils are insoluble in water and are soluble in alcohol, ether, fixed oils (vegetal), and other organic solvents. Typical physical characteristics found in essential oils include boiling points that vary from about 160° to 240° C. and densities ranging from about 0.759 to about 1.096.

Essential oils typically are named by the plant from which the oil is found. For example, rose oil or peppermint oil are derived from rose or peppermint plants, respectively. Non-limiting examples of essential oils that can be used in the context of the present invention include sesame oil, *macadamia* nut oil, tea tree oil, evening primrose oil, Spanish sage oil, Spanish rosemary oil, coriander oil, thyme oil, pimento berries oil, rose oil, anise oil, balsam oil, bergamot oil, rosewood oil, cedar oil, chamomile oil, sage oil, clary sage oil, clove oil, cypress oil, *eucalyptus* oil, fennel oil, sea fennel oil, frankincense oil, *geranium* oil, ginger oil, grapefruit oil, jasmine oil, juniper oil, lavender oil, lemon oil, lemongrass oil, lime oil, mandarin oil, marjoram oil, myrrh oil, neroli oil, orange oil, patchouli oil, pepper oil, black pepper oil, petitgrain oil, pine oil, rose otto oil, rosemary oil, sandalwood oil, spearmint oil, spikenard oil, vetiver oil, wintergreen oil, or ylang ylang. Other essential oils known to those of skill in the art are also contemplated as being useful within the context of the present invention.

h. Thickening Agents

Thickening agents, including thickener or gelling agents, include substances which that can increase the viscosity of a composition. Thickeners includes those that can increase the viscosity of a composition without substantially modifying the efficacy of the active ingredient within the composition. Thickeners can also increase the stability of the compositions of the present invention. In certain aspects of the present invention, thickeners include hydrogenated polyisobutene, trihydroxystearin, ammonium acryloyldimethyltaurate/vp copolymer, or a mixture of them.

Non-limiting examples of additional thickening agents that can be used in the context of the present invention include carboxylic acid polymers, crosslinked polyacrylate polymers, polyacrylamide polymers, polysaccharides, and gums. Examples of carboxylic acid polymers include crosslinked compounds containing one or more monomers derived from acrylic acid, substituted acrylic acids, and salts and esters of these acrylic acids and the substituted acrylic acids, wherein the crosslinking agent contains two or more carbon-carbon double bonds and is derived from a polyhydric alcohol (see U.S. Pat. Nos. 5,087,445; 4,509,949; 2,798,053; CTFA International Cosmetic Ingredient Dictionary, Fourth edition, 1991, pp. 12 and 80). Examples of commercially available carboxylic acid polymers include carbomers, which are homopolymers of acrylic acid crosslinked with allyl ethers of sucrose or pentaerytritol (e.g., Carbopol™ 900 series from B. F. Goodrich).

Non-limiting examples of crosslinked polyacrylate polymers include cationic and nonionic polymers. Examples are described in U.S. Pat. Nos. 5,100,660; 4,849,484; 4,835,206; 4,628,078; 4,599,379).

Non-limiting examples of polyacrylamide polymers (including nonionic polyacrylamide polymers including substituted branched or unbranched polymers) include polyacrylamide, isoparaffin and laureth-7, multi-block copolymers of acrylamides and substituted acrylamides with acrylic acids and substituted acrylic acids.

Non-limiting examples of polysaccharides include cellulose, carboxymethyl hydroxyethylcellulose, cellulose acetate propionate carboxylate, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, and mixtures thereof. Another example is an alkyl substituted cellulose where the hydroxy groups of the cellulose polymer is hydroxyalkylated (preferably hydroxy ethylated or hydroxypropylated) to form a hydroxyalkylated cellulose which is then further modified with a C10-C30 straight chain or branched chain alkyl group through an ether linkage. Typically these polymers are ethers of C10-C30 straight or branched chain alcohols with hydroxyalkylceluloses. Other useful polysaccharides include scleroglucans comprising a linear chain of (1-3) linked glucose units with a (1-6) linked glucose every three unit.

Non-limiting examples of gums that can be used with the present invention include acacia, agar, algin, alginic acid, ammonium alginate, amylopectin, calcium alginate, calcium carrageenan, camitine, carrageenan, dextrin, gelatin, gellan gum, guar gum, guar hydroxypropyltrimonium chloride, hectorite, hyaluronic acid, hydrated silica, hydroxypropyl chitosan, hydroxypropyl guar, karaya gum, kelp, locust bean gum, natto gum, potassium alginate, potassium carrageenan, propylene glycol alginate, sclerotium gum, sodium carboxymethyl dextran, sodium carrageenan, tragacanth gum, xanthan gum, and mixtures thereof.

i. Preservatives

Non-limiting examples of preservatives that can be used in the context of the present invention include quaternary ammonium preservatives such as polyquatemium-1 and benzalkonium halides (e.g., benzalkonium chloride ("BAC") and benzalkonium bromide), parabens (e.g., methylparabens and propylparabens), phenoxyethanol, benzyl alcohol, chlorobutanol, phenol, sorbic acid, thimerosal or combinations thereof.

2. Pharmaceutical Ingredients

Pharmaceutical active agents are also contemplated as being useful with the compositions of the present invention. Non-limiting examples of pharmaceutical active agents include anti-acne agents, agents used to treat rosacea, analgesics, anesthetics, anorectals, antihistamines, anti-inflammatory agents including non-steroidal anti-inflammatory drugs, antibiotics, antifungals, antivirals, antimicrobials, anti-cancer actives, scabicides, pediculicides, antineoplastics, antiperspirants, antipruritics, antipsoriatic agents, antiseborrheic agents, biologically active proteins and peptides, burn treatment agents, cauterizing agents, depigmenting agents, depilatories, diaper rash treatment agents, enzymes, hair growth stimulants, hair growth retardants including DFMO and its salts and analogs, hemostatics, kerotolytics, canker sore treatment agents, cold sore treatment agents, dental and periodontal treatment agents, photosensitizing actives, skin protectant/barrier agents, steroids including hormones and corticosteroids, sunburn treatment agents, sunscreen agents, transdermal actives, nasal actives, vaginal actives, wart treatment agents, wound treatment agents, wound healing agents, etc.

G. KITS

Kits are also contemplated as being used in certain aspects of the present invention. For instance, compositions of the present invention can be included in a kit. A kit can include a container. Containers can include a bottle, a metal tube, a laminate tube, a plastic tube, a dispenser, a pressurized container, a barrier container, a package, a compartment, a lipstick container, a compact container, cosmetic pans that can hold cosmetic compositions, or other types of containers such as injection or blow-molded plastic containers into which the dispersions or compositions or desired bottles, dispensers, or packages are retained. The kit and/or container can include indicia on its surface. The indicia, for example, can be a word, a phrase, an abbreviation, a picture, or a symbol.

The containers can dispense a pre-determined amount of the composition. In other embodiments, the container can be squeezed (e.g., metal, laminate, or plastic tube) to dispense a desired amount of the composition. The composition can be dispensed as a spray, an aerosol, a liquid, a fluid, or a semi-solid. The containers can have spray, pump, or squeeze mechanisms. A kit can also include instructions for employing the kit components as well the use of any other compositions included in the container. Instructions can include an explanation of how to apply, use, and maintain the compositions.

H. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

1. Example 1

Formulations having the ingredients from Example 1 were prepared as topical skin and/or hair compositions. The formulation in Table 1 was prepared as a moisturizer. The formulation in Table 2 was prepared as a mask. The formulation in Table 3 was prepared as a foundation. The formulation in Table 4 was prepared as a freshener. The formulations in Tables 5 and 6 were prepared as cleansers.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

TABLE 1*

| Ingredient | % Concentration (by weight) |
| --- | --- |
| Water | 63 |
| Glycerin | 11 |
| Cyclopentasiloxane | 5 |
| Hydrogenated polyisobutene | 3 |
| Butylene glycol | 3 |
| Dimethicone | 3 |
| Octyldodecyl myristate | 2 |
| Arachidyl alcohol | 2 |
| Glyceryl stearate | 2 |
| Cetearyl alcohol | 1 |
| Petrolatum | 1 |
| PEG-100 stearate | 1 |
| Behenyl alcohol | 0.9 |
| Phenoxyethanol | 0.9 |
| Ammonium acryloyldimethyltaurate/VP copolymer | 0.7 |
| Arachidyl glucoside | 0.5 |
| Dimethicone/vinyl dimethicone crosspolymer | 0.3 |
| Chlorphenesin | 0.2 |
| Disodium EDTA | 0.1 |
| Hydrolyzed algae extract | 0.1 |
| Saccharide isomerate | 0.01 |
| Fragrance (optional) | 0.2 |
| *Opuntia tuna* fruit extract (optional) | 0.0005 |
| Excipients** | q.s. |

*Formulation can be prepared by mixing the ingredients in a beaker under heat 70-75° C. until homogenous. Subsequently, the formulation can be cooled to standing room temperature (20-25° C.). Further, and if desired, additional ingredients can be added, for example, to modify the rheological properties of the composition.
**Excipients can be added, for example, to modify the rheological properties of the composition. Alternatively, the amount of water can be varied so long as the amount of water in the composition is at least 50% w/w, and preferably between 55 to 70% w/w.

TABLE 2*

| Ingredient | % Concentration (by weight) |
| --- | --- |
| Water | 77 |
| Glyceryl stearate | 6 |
| Glycerin | 4 |
| Petrolatum | 3 |
| Stearic acid | 2 |
| Cetyl alcohol | 2 |
| Lauryl methacrylate/glycol dimethacrylate crosspolymer | 1 |
| Stearyl alcohol | 1 |
| Phenoxyethanol | 0.9 |
| Triethanolamine | 0.9 |
| Dimethicone | 0.7 |
| Titanium dioxide | 0.5 |
| Betaine | 0.5 |
| Fragrance (optional) | 0.3 |
| Carbomer | 0.2 |
| Behenyl alcohol | 0.2 |
| Disodium EDTA | 0.1 |
| Hydrolyzed algae extract | 0.1 |
| Palmitic acid | 0.1 |
| Saccharide isomerate | 0.01 |
| *Opuntia tuna* fruit extract (optional) | 0.0005 |
| Excipients** | q.s. |

*Formulation can be prepared by mixing the ingredients in a beaker under heat 70-75° C. until homogenous. Subsequently, the formulation can be cooled to standing room temperature (20-25° C.). Further, and if desired, additional ingredients can be added, for example, to modify the rheological properties of the composition.
**Excipients can be added, for example, to modify the rheological properties of the composition. Alternatively, the amount of water can be varied so long as the amount of water in the composition is at least 60% w/w, and preferably between 60 to 75% w/w.

TABLE 3*

| Ingredient | % Concentration (by weight) |
| --- | --- |
| Water | 37 |
| Propanediol | 13 |
| Caprylic/capric triglyceride | 8 |
| Octinoxate | 7 |
| Glycerin | 6 |
| Silica | 5 |
| Homosalate | 4 |
| Cetearyl alcohol | 2 |
| Oxybenzone | 2 |
| *Butyrospermum parkii* (shea) butter | 1 |
| Glyceryl stearate | 1 |
| Phenoxyethanol | 0.8 |
| PEG-100 stearate | 0.7 |
| Hydroxyethyl acrylate/sodium acryloyldimethyl taurate copolymer | 0.7 |
| Bis-diglyceryl polyacyladipate-2 | 0.5 |
| Squalane | 0.5 |
| Fragrance (optional) | 0.5 |
| Isohexadecane | 0.4 |
| Caprylyl glycol | 0.3 |
| Chlorphenesin | 0.2 |
| Tocopherol | 0.1 |
| Dipotassium glycyrrhizate | 0.1 |
| Polysorbate 60 | 0.1 |
| Hydrolyzed algae extract | 0.01 |
| Saccharide isomerate | 0.001 |
| *Opuntia tuna* fruit extract (optional) | 0.0005 |
| Excipients** | q.s. |

*Formulation can be prepared by mixing the ingredients in a beaker under heat 70-75° C. until homogenous. Subsequently, the formulation can be cooled to standing room temperature (20-25° C.). Further, and if desired, additional ingredients can be added, for example, to modify the rheological properties of the composition.
**Excipients can be added, for example, to modify the rheological properties of the composition. Alternatively, the amount of water can be varied so long as the amount of water in the composition is at least 25% w/w, and preferably between 30 to 50% w/w.

TABLE 4*

| Ingredient | % Concentration (by weight) |
|---|---|
| Water | 93 |
| Glycerin | 5 |
| Phenoxyethanol | 0.9 |
| PEG-40 hydrogenated castor oil | 0.4 |
| Chlorphenesin | 0.2 |
| Carbomer | 0.2 |
| Polysorbate 20 | 0.2 |
| Triethanolamine | 0.1 |
| Hydrolyzed jojoba esters | 0.1 |
| Hydrolyzed algae extracts | 0.1 |
| Fragrance (optional) | 0.1 |
| Saccharide isomerate | 0.01 |
| *Opuntia tuna* fruit extract (optional) | 0.0005 |
| Excipients** | q.s. |

*Formulation can be prepared by mixing the ingredients in a beaker under heat 70-75° C. until homogenous. Subsequently, the formulation can be cooled to standing room temperature (20-25° C.). Further, and if desired, additional ingredients can be added, for example, to modify the rheological properties of the composition.
**Excipients can be added, for example, to modify the rheological properties of the composition. Alternatively, the amount of water can be varied so long as the amount of water in the composition is at least 70% w/w, and preferably between 80 to 95% w/w.

TABLE 5*

| Ingredient | % Concentration (by weight) |
|---|---|
| Water | 72 |
| Petrolatum | 6 |
| Glycerin | 4 |
| PEG-6 caprylic/capric glycerides | 3 |
| Glyceryl stearate | 3 |
| *Butyrospermum parkii* (shea) butter | 3 |
| Cetyl alcohol | 2 |
| Stearyl alcohol | 1 |
| Propylene glycol | 0.8 |
| Phenoxyethanol | 0.7 |
| Cetearyl alcohol | 0.6 |
| Triethanolamine | 0.5 |
| Pentaerythrityl tetraisostearate | 0.5 |
| Betaine | 0.5 |
| Fragrance (optional) | 0.5 |
| Ceteth-20 phosphate | 0.4 |
| Methylparaben | 0.4 |
| Hydroxypropyl methylcellulose | 0.3 |
| Dicetyl phosphate | 0.2 |
| Dimethicone | 0.2 |
| BHT | 0.2 |
| Carbomer | 0.1 |
| Hydroxypropyl cyclodextrin | 0.1 |
| Disodium EDTA | 0.1 |
| Dipotassium glycyrrhizate | 0.1 |
| Hydrolyzed algae extract | 0.1 |
| Saccharide isomerate | 0.01 |
| *Opuntia tuna* fruit extract (optional) | 0.0005 |
| Excipients** | q.s. |

*Formulation can be prepared by mixing the ingredients in a beaker under heat 70-75° C. until homogenous. Subsequently, the formulation can be cooled to standing room temperature (20-25° C.). Further, and if desired, additional ingredients can be added, for example, to modify the rheological properties of the composition.
**Excipients can be added, for example, to modify the rheological properties of the composition. Alternatively, the amount of water can be varied so long as the amount of water in the composition is at least 60% w/w, and preferably between 65 to 85% w/w.

TABLE 6*

| Ingredient | % Concentration (by weight) |
|---|---|
| Water | 72 |
| Petrolatum | 6 |
| Glycerin | 4 |
| PEG-6 caprylic/capric glycerides | 3 |
| Glyceryl stearate | 3 |
| *Butyrospermum parkii* (shea) butter | 3 |
| Cetyl alcohol | 2 |
| Stearyl alcohol | 1 |
| Phenoxyethanol | 0.6 |
| Cetearyl alcohol | 0.6 |
| Propylene glycol | 0.5 |
| Triethanolamine | 0.5 |
| Pentaerythrityl tetraisostearate | 0.5 |
| Betaine | 0.5 |
| Fragrance (optional) | 0.5 |
| Ceteth-20 phosphate | 0.4 |
| Hydroxypropyl methylcellulose | 0.3 |
| Methylparaben | 0.2 |
| Dicetyl phosphate | 0.2 |
| Caprylyl glycol | 0.2 |
| Dimethicone | 0.2 |
| BHT | 0.2 |
| Carbomer | 0.1 |
| Hydroxypropyl cyclodextrin | 0.1 |
| Disodium EDTA | 0.1 |
| Dipotassium glycyrrhizate | 0.1 |
| Decylene glycol | 0.1 |
| Hydrolyzed algae extract | 0.1 |
| Saccharide isomerate | 0.01 |
| *Opuntia tuna* fruit extract (optional) | 0.0005 |
| Excipients** | q.s. |

*Formulation can be prepared by mixing the ingredients in a beaker under heat 70-75° C. until homogenous. Subsequently, the formulation can be cooled to standing room temperature (20-25° C.). Further, and if desired, additional ingredients can be added, for example, to modify the rheological properties of the composition.
**Excipients can be added, for example, to modify the rheological properties of the composition. Alternatively, the amount of water can be varied so long as the amount of water in the composition is at least 60% w/w, and preferably between 65 to 85% w/w.

2. Example 2

(Efficacy of Ingredients)

The efficacy of the ingredients were determined by the following methods. The following are non-limiting assays that can be used in the context of the present invention. It should be recognized that other testing procedures can be used, including, for example, objective and subjective procedures.

It was determined that saccharide isomerate increases keratinocyte production of filaggrin, increases conductance of artificial skin equivalents, increases keratinocyte production of occludin, inhibits TNFα production from keratinocytes, and has antioxidant capacity. It was also determined that hydrolyzed algae extract increases keratinocyte production of filaggrin, increases conductance of artificial skin equivalents, increases keratinocyte production of occludin, and decreases keratinocyte monolayer permeability. A summary of quantitative results is found in Table 7 and the method used to determine the properties of the extracts are provided below.

TABLE 7

| Assay | Ingredient | Activity |
|---|---|---|
| Keratinocyte Production of Filaggrin | Saccharide isomerate | +28% |
|  | Hydrolyzed algae extract | +32% |
| Artificial Skin Moisturization/Hydration | Saccharide isomerate | +79% |
|  | Hydrolyzed algae extract | +240% |
| Keratinocyte Production of Occludin | Saccharide isomerate | +170% |
|  | Hydrolyzed algae extract | +39% |
| Keratinocyte Production of TNFα | Saccharide isomerate | −88% |
| Antioxidant Capacity | Saccharide isomerate | +36% |
| Keratinocyte Monolayer Permeability | Hydrolyzed algae extract | −30% |

Production of Filaggrin—

Saccharide isomerate and hydrolyzed algae extract have each been shown to increase keratinocyte production of filaggrin. Filaggrin is the precursor to Natural Moisturizing Factor (NMF) in the skin. Increased NMF increases the moisture content of the skin. Filaggrin production in treated and non-treated keratinocytes were determined using a bioassay that analyzes filaggrin concentration in keratinocyte cell lysates. The bioassay was performed using PROTEIN-SIMPLE® Simon™ western blotting protocol. It was determined that saccharide isomerate and Hydrolyzed algae extract increased keratinocyte production of filaggrin by 28% and 32%, respectively.

For the samples, normal human epidermal keratinocytes (NHEK) were grown in EPI-200-Mattek Epilife® growth media with calcium from Life Technologies (M-EP-500-CA). NHEK were incubated in growth medium overnight at 37° C. in 5% $CO_2$ prior to treatment. NHEK were then incubated in growth medium with or without 1% test compound/extract for 24 to 36 hours. The NHEK were then washed, collected, and stored on ice or colder until lysed on ice using a lysis buffer and sonication. The protein concentrations of the samples were determined and used to normalize the samples. The lysates were stored at −80° C. until use in the bioassay.

Briefly, the bioassay assay employs a quantitative western blotting immunoassay technique using an antibody specific for filaggrin to quantitatively detect filaggrin in the test samples. Cell samples were lysed and normalized for protein concentration. Normalized samples and molecular weight standards were then loaded and ran on a denatured protein separation gel using capillary electrophoresis. The proteins in the gel were immobilized and immunoprobed using a primary antibody specific for filaggrin. The immobilized proteins were then immunoprobed with an enzyme-linked detection antibody that binds the primary antibody. A chemiluminescent substrate solution was then added to the immobilized proteins to allow chemiluminescent development in proportion to the amount of filaggrin bound in the immobilization. The chemiluminescent development was stopped at a specific time and the intensity of the chemiluminescent signal was measured and compared to positive and negative controls.

Skin Moisturization/Hydration—

Saccharide isomerate and hydrolyzed algae extract each have been shown to increase a clinical measurement of skin moisturization using a skin moisture/hydration assay. This assay determines impedance measurements with the Nova Dermal Phase Meter. The impedance meter measures changes in skin moisture content. The outer layer of the skin has distinct electrical properties. When skin is dry it conducts electricity very poorly. As it becomes more hydrated increasing conductivity results. Consequently, changes in skin impedance (related to conductivity) can be used to assess changes in skin hydration. It was determined that saccharide isomerate and Hydrolyzed algae extract increased conductance of artificial skin by 79% and 240%, respectively, indicating increased moisture/hydration.

For this assay, treated and non-treated artificial skin equivalents were used. The Nova Dermal Phase Meter was calibrated according to instrument instructions for each testing day. A notation of temperature and relative humidity was made for comparison purposes. Impedance was evaluated as follows: prior to measurement, the samples were equilibrate in a room with defined humidity (e.g., 30-50%) and temperature (e.g., 68-72° C.). Impedance readings were taken on each sample, recorded, and averaged. The T5 setting were used on the impedance meter which averages the impedance values of every five seconds application to the sample. Changes were reported with statistical variance and significance.

Production of Occludin—

Saccharide isomerate has been shown to increase keratinocyte production of occludin. Occludin is a protein critical to the formulation of tight junctions and the skin's moisture barrier function. Occludin production in treated and non-treated keratinocytes were determined using a bioassay that analyzes occludin concentration in keratinocyte cell lysates. The bioassay was performed using PROTEIN-SIMPLE® Simon™ western blotting protocol. It was determined that saccharide isomerate and hydrolyzed algae extract increased keratinocyte production of occludin by 170% and 39% respectively.

For the samples, adult human epidermal keratinocytes (HEKa) from Life Technologies (C-005-5C) were grown at 37° C. and 5% C02 for 24 hours in Epilife growth media with calcium from Life Technologies (M-EP-500-CA) supplemented with Keratinocyte Growth Supplement (HKGS) from Life Technologies (S-101-5). HEKa were then incubated in growth medium with test compound/extract, no compound/extract for negative control, or with 1 mM $CaCl_2$ for positive control for 24 to 48 hours. The HEKa were then washed, collected, and stored on ice or colder until lysed on ice using a lysis buffer and sonication. The protein concentrations of the samples were determined and used to normalize the samples. The lysates were stored at −80° C. until use in the bioassay.

Briefly, the bioassay assay employs a quantitative western blotting immunoassay technique using an antibody specific for occludin to quantitatively detect occludin in the test samples. Cell samples were lysed and normalized for protein concentration. Normalized samples and molecular weight standards were then loaded and ran on a denatured protein separation gel using capillary electrophoresis. The proteins in the gel were immobilized and immunoprobed using a primary antibody specific for occludin. The immobilized proteins were then immunoprobed with an enzyme-linked detection antibody that binds the primary antibody. A chemiluminescent substrate solution was then added to the immobilized proteins to allow chemiluminescent development in proportion to the amount of occludin bound in the immobilization. The chemiluminescent development was stopped at a specific time and the intensity of the chemiluminescent signal was measured and compared to positive and negative controls.

Inhibition of Tumor Necrosis Factor Alpha (TNF-α)—

Saccharide isomerate has been shown to inhibit TNF-α production in keratinocytes. TNF-α is the prototype ligand of the TNF superfamily. It is a pleiotropic cytokine that plays a central role in inflammation. Increase in its expression is associated with an up regulation in pro-inflammatory activity. The bioassay used to analyze the effect of saccharide isomerate used a spectrophotometric measurement that reflects the presence of TNF-α and cellular viability. It was determined that saccharide isomerate inhibits TNF-α production in keratinocytes by 88%.

Subconfluent normal human adult keratinocytes (Cascade Biologics) cultivated in EpiLife standard growth medium (Cascade Biologics) at 37° C. in 5% $CO_2$, were treated with phorbol 12-myristate 13-acetate (PMA, 10 ng/ml, Sigma Chemical, # P1585-1MG) and either saccharide isomerate (treated sample) or no additional treatment (untreated sample) for 6 hours. PMA causes a dramatic increase in TNF-α secretion which peaks at 6 hours after treatment. Following incubation, cell culture medium was collected and the amount of TNF-α secretion quantified using a sandwich enzyme linked immuno-sorbant assay (ELISA) from R&D Systems (# DTA00C).

Briefly, the ELISA assay employed the quantitative sandwich enzyme immunoassay technique whereby a monoclonal antibody specific for TNF-α was been pre-coated onto a microplate. Standards and treated and untreated samples were pipetted into the microplate wells to allow any TNF-α present to be bound by the immobilized antibody. After washing away any unbound substances, an enzyme-linked polyclonal antibody specific for TNF-α was added to the wells. Following a wash to remove any unbound antibody-enzyme reagent, a substrate solution was added to the wells to allow color development in proportion to the amount of TNF-α bound in the initial step. The color development was stopped at a specific time and the intensity of the color at 450 nm was measured using a microplate reader.

Antioxidant Capacity—

Saccharide isomerate has been shown to possess antioxidant capacity. The antioxidant system of living organisms includes enzymes such as superoxide dismutase, catalase, and glutathione peroxidase; macromolecules such as albumin, ceruloplasmin, and ferritin; and an array of small molecules, including ascorbic acid, α-tocopherol, β-carotene, reduced glutathione, uric acid, and bilirubin. The sum of endogenous and food-derived antioxidants represents the total antioxidant activity of the extracellular fluid. Cooperation of all the different antioxidants provides greater protection against attack by reactive oxygen or nitrogen radicals, than any single compound alone. Thus, the overall antioxidant capacity may give more relevant biological information compared to that obtained by the measurement of individual components, as it accounts for the cumulative effect of all antioxidants present in plasma and body fluids. It was determined that saccharide isomerate possesses an antioxidant capacity of 36% of trolox. Antioxidant capacity indicates a capability to reduce oxidizing agents (oxidants).

Antioxidant capacity was determined by an Oxygen Radical Absorption (or Absorbance) Capacity (ORAC) assay. This assay quantifies the degree and length of time it takes to inhibit the action of an oxidizing agent, such as oxygen radicals, that are known to cause damage to cells (e.g., skin cells). The ORAC value of control and Saccharide isomerate was determined by the Zen-Bio ORAC Anti-oxidant Assay kit (# AOX-2). Briefly, this assay measures the loss of fluorescein fluorescence over time due to the peroxyl-radical formation by the breakdown of AAPH (2,2'-axobis-2-methyl propanimidamide, dihydrochloride). Trolox, a water soluble vitamin E analog, serves as positive control inhibition fluorescein decay in a dose dependent manner.

Decreases Keratinocyte Monolayer Permeability—

Hydrolyzed algae extract has been shown to decrease keratinocyte monolayer permeability. This is a measure of skin barrier integrity. Keratinocyte monolayer permeability in treated and non-treated keratinocytes were determined using the In Vitro Vascular Permeability assay by Millipore (ECM642). This assay analyzes endothelial cell adsorption, transport and permeability. It was determined that hydrolyzed algae extract decreases keratinocyte monolayer permeability by 30%.

Samples were tested according to the In Vitro Vascular Permeability assay manufacturer's instructions. Briefly, adult human epidermal keratinocytes from Life Technologies (C-005-5C) were seeded onto a porous collagen-coated membrane within a collection well. The keratinocytes were incubated in Epilife growth media with calcium from Life Technologies (M-EP-500-CA) supplemented with Keratinocyte Growth Supplement (HKGS) from Life Technologies (S-101-5) for 24 hours at 37° C. and 5% $CO_2$. This incubation time allowed the cells to form a monolayer and occlude the membrane pores. The media was then replaced with fresh media with (test sample)/without (non-treated control) test compounds/extracts and the keratinocytes were incubated for an additional 48 hours at 37° C. and 5% $CO_2$. To determine permeability of the keratinocyte monolayer after incubation with/without the test compound/extract, the media is replaced with fresh media containing a high molecular weight Fluorescein isothiocyanate (FITC)-Dextran and the keratinocytes are incubated for 4 hours at 37° C. and 5% $CO_2$. During the 4 hours incubation, FITC passed through the keratinocytes monolayer and porous membrane into the collection well at a rate proportional to the monolayer's permeability. After the 4 hour incubation, cell viability and the content of FITC in the collection wells was determined. For the FITC content, the media in the collection well was collected and fluorescence of the media determined at 480 nm (Em) when excited at 520 nm. Percent permeability and percent change in comparison to the non-treated controls were determined by the following equations: Percent Permeability=((Mean Ex/Em of test sample)/Mean Ex/Em untreated control)*100; Percent Change=Percent Permeability of test sample—Percent Permeability of untreated control.

3. Example 3

(Additional Assays)

Assays that can be used to determine the efficacy of any one of the ingredients or any combination of ingredients or compositions having said combination of ingredients disclosed throughout the specification and claims can be determined by methods known to those of ordinary skill in the art. The following are non-limiting assays that can be used in the context of the present invention. It should be recognized that other testing procedures can be used, including, for example, objective and subjective procedures.

B16 Pigmentation Assay:

Melanogenesis is the process by which melanocytes produce melanin, a naturally produced pigment that imparts color to skin, hair, and eyes. Inhibiting melanogenesis is beneficial to prevent skin darkening and lighten dark spots associated with aging. This bioassay utilizes B16-F1 melanocytes (ATCC), an immortalized mouse melanoma cell line, to analyze the effect of compounds on melanogenesis. The endpoint of this assay is a spectrophotometric measurement of melanin production and cellular viability. B16-F1 melanocytes, can be cultivated in standard DMEM growth medium with 10% fetal bovine serum (Mediatech) at 37° C. in 10% $CO_2$ and then treated with any one of the active ingredients, combination of ingredients, or compositions having said combinations disclosed in the specification for 6 days. Following incubation, melanin secretion is measured by absorbance at 405 nm and cellular viability is quantified.

Collagen Stimulation Assay:

Collagen is an extracellular matrix protein critical for skin structure. Increased synthesis of collagen helps improve skin firmness and elasticity. This bioassay can be used to examine the effect of any one of the active ingredients, combination of ingredients, or compositions having said combinations disclosed in the specification on the production of procollagen peptide (a precursor to collagen) by human epidermal fibroblasts. The endpoint of this assay is a spectrophotometric measurement that reflects the presence of procollagen peptide and cellular viability. The assay employs the quantitative sandwich enzyme immunoassay technique whereby a monoclonal antibody specific for procollagen peptide has been pre-coated onto a microplate. Standards and samples can be pipetted into the wells and any procollagen peptide present is bound by the immobilized antibody. After washing away any unbound substances, an enzyme-linked polyclonal antibody specific for procollagen peptide can be added to the wells. Following a wash to remove any unbound antibody-enzyme reagent, a substrate solution can be added to the wells and color develops in proportion to the amount of procollagen peptide bound in the initial step using a microplate reader for detection at 450 nm. The color development can be stopped and the intensity of the color can be measured. Subconfluent normal human adult epidermal fibroblasts (Cascade Biologics) cultivated in standard DMEM growth medium with 10% fetal bovine serum (Mediatech) at 37° C. in 10% C02, can be treated with each of the combination of ingredients or compositions having said combinations disclosed in the specification for 3 days. Following incubation, cell culture medium can be collected and the amount of procollagen peptide secretion quantified using a sandwich enzyme linked immuno-sorbant assay (ELISA) from Takara (# MK101).

Elastin Stimulation Assay:

Elastin is a connective tissue protein that helps skin resume shape after stretching or contracting. Elastin is also an important load-bearing protein used in places where mechanical energy is required to be stored. Elastin is made by linking many soluble tropoelastin protein molecules, in a reaction catalyzed by lysyl oxidase. Elastin secretion and elastin fibers can be monitored in cultured human fibroblasts by staining of cultured human fibroblasts using immunofluorescent antibodies directed against elastin.

Laminin Stimulation Assay:

Laminin and fibronectin are major proteins in the dermal-epidermal junction (DEJ) (also referred to as the basement membrane). The DEJ is located between the dermis and the epidermis interlocks forming fingerlike projections called rete ridges. The cells of the epidermis receive their nutrients from the blood vessels in the dermis. The rete ridges increase the surface area of the epidermis that is exposed to these blood vessels and the needed nutrients. The DEJ provides adhesion of the two tissue compartments and governs the structural integrity of the skin. Laminin and fibronectin are two structural glycoproteins located in the DEJ. Considered the glue that holds the cells together, laminin and fibronectin are secreted by dermal fibroblasts to help facilitate intra- and inter-cellular adhesion of the epidermal calls to the DEJ. Laminin secretion can be monitored by quantifying laminin in cell supernatants of cultured human fibroblasts treated for 3 days with culture medium with or without 1.0% final concentration of the test ingredient(s). Following incubation, laminin content can be measured using immunofluorescent antibodies directed against laminin in an enzyme linked immuno-sorbant assay (ELISA). Measurements are normalized for cellular metabolic activity, as determined by bioconversion of 3-(4,5-dimethylthiazol-2-yl)-5-(3-carboxymethoxyphenyl)-2-(4-sulfophenyl)-2H-tetrazolium (MTS).

Antioxidant (AO) Assay:

An in vitro bioassay that measures the total anti-oxidant capacity of any one of the ingredients, combination of ingredients, or compositions having said combinations disclosed in the specification. The assay relies on the ability of antioxidants in the sample to inhibit the oxidation of ABTS® (2,2'-azino-di-[3-ethylbenzthiazoline sulphonate]) to ABTS®•+ by metmyoglobin. The antioxidant system of living organisms includes enzymes such as superoxide dismutase, catalase, and glutathione peroxidase; macromolecules such as albumin, ceruloplasmin, and ferritin; and an array of small molecules, including ascorbic acid, α-tocopherol, β-carotene, reduced glutathione, uric acid, and bilirubin. The sum of endogenous and food-derived antioxidants represents the total antioxidant activity of the extracellular fluid. Cooperation of all the different antioxidants provides greater protection against attack by reactive oxygen or nitrogen radicals, than any single compound alone. Thus, the overall antioxidant capacity may give more relevant biological information compared to that obtained by the measurement of individual components, as it considers the cumulative effect of all antioxidants present in plasma and body fluids. The capacity of the antioxidants in the sample to prevent ABTS oxidation is compared with that of Trolox, a water-soluble tocopherol analogue, and is quantified as molar Trolox equivalents. Anti-Oxidant capacity kit #709001 from Cayman Chemical (Ann Arbor, Mich. USA) can be used as an in vitro bioassay to measure the total anti-oxidant capacity of each of any one of the active ingredients, combination of ingredients, or compositions having said combinations disclosed in the specification. The protocol can be followed according to manufacturer recommendations. The assay relied on antioxidants in the sample to inhibit the oxidation of ABTS® (2,2'-azino-di-[3-ethylbenzthiazoline sulphonate]) to ABTS®•+ by metmyoglobin. The capacity of the antioxidants in the sample to prevent ABTS oxidation can be compared with that Trolox, a water-soluble tocopherol analogue, and can be quantified as a molar Trolox equivalent.

Mushroom Tyrosinase Activity Assay:

In mammalian cells, tyrosinase catalyzes two steps in the multi-step biosynthesis of melanin pigments from tyrosine (and from the polymerization of dopachrome). Tyrosinase is localized in melanocytes and produces melanin (aromatic quinone compounds) that imparts color to skin, hair, and eyes. Purified mushroom tyrosinase (Sigma) can be incubated with its substrate L-Dopa (Fisher) in the presence or absence of each of the active ingredients, any one of the combination of ingredients, or compositions having said combinations disclosed in the specification. Pigment formation can be evaluated by colorimetric plate reading at 490 nm. The percent inhibition of mushroom tyrosinase activity can be calculated compared to non-treated controls to determine the ability of test ingredients or combinations thereof to inhibit the activity of purified enzyme. Test extract inhibition was compared with that of kojic acid (Sigma).

Matrix Metalloproteinase 3 and 9 Enzyme Activity (MMP3; MMP9) Assay:

An in vitro matrix metalloprotease (MMP) inhibition assay. MMPs are extracellular proteases that play a role in many normal and disease states by virtue of their broad substrate specificity. MMP3 substrates include collagens, fibronectins, and laminin; while MMP9 substrates include collagen VII, fibronectins and laminin. Using Colorimetric Drug Discovery kits from BioMol International for MMP3 (AK-400) and MMP-9 (AK-410), this assay is designed to measure protease activity of MMPs using a thiopeptide as a chromogenic substrate (Ac-PLG-[2-mercapto-4-methylpentanoyl]-LG-OC2H5)5,6. The MMP cleavage site peptide bond is replaced by a thioester bond in the thiopeptide. Hydrolysis of this bond by an MMP produces a sulfhydryl group, which reacts with DTNB [5,5'-dithiobis(2-nitrobenzoic acid), Ellman's reagent] to form 2-nitro-5-thiobenzoic acid, which can be detected by its absorbance at 412 nm ($\varepsilon$=13,600 M-1 cm-1 at pH 6.0 and above 7). The active ingredients, any one of the combination of ingredients, or compositions having said combinations disclosed in the specification can be assayed.

Matrix Metalloproteinase 1 Enzyme Activity (MMP1) Assay:

An in vitro matrix metalloprotease (MMP) inhibition assay. MMPs are extracellular proteases that play a role in many normal and disease states by virtue of their broad substrate specificity. MMP1 substrates include collagen IV. The Molecular Probes Enz/Chek Gelatinase/Collagenase Assay kit (# E12055) utilizes a fluorogenic gelatin substrate to detect MMP1 protease activity. Upon proteolytic cleavage, bright green fluorescence is revealed and may be monitored using a fluorescent microplate reader to measure enzymatic activity. The Enz/Chek Gelatinase/Collagenase Assay kit (# E12055) from Invitrogen is designed as an in vitro assay to measure MMP1 enzymatic activity. The active ingredients, any one of the combination of ingredients, or compositions having said combinations disclosed in the specification can be assayed. The assay relies upon the ability of purified MMP1 enzyme to degrade a fluorogenic gelatin substrate. Once the substrate is specifically cleaved by MMP1 bright green fluorescence is revealed and may be monitored using a fluorescent microplate reader. Test materials are incubated in the presence or absence of the purified enzyme and substrate to determine their protease inhibitor capacity.

Cyclooxygenase (COX) Assay:

An in vitro cyclooxygenase-1 and -2 (COX-1, -2) inhibition assay. COX is a bifunctional enzyme exhibiting both cyclooxygenase and peroxidase activities. The cyclooxygenase activity converts arachidonic acid to a hydroperoxy endoperoxide (Prostaglandin G2; PGG2) and the peroxidase component reduces the endoperoxide (Prostaglandin H2; PGH2) to the corresponding alcohol, the precursor of prostaglandins, thromboxanes, and prostacyclins. This COX Inhibitor screening assay measures the peroxidase component of cyclooxygenases. The peroxidase activity is assayed colorimetrically by monitoring the appearance of oxidized N,N,N',N'-tetramethyl-p-phenylenediamine (TMPD). This inhibitor screening assay includes both COX-1 and COX-2 enzymes in order to screen isozyme-specific inhibitors. The Colormetric COX (ovine) Inhibitor screening assay (#760111, Cayman Chemical) can be used to analyze the effects of each of the active ingredients, any one of the combination of ingredients, or compositions having said combinations disclosed in the specification on the activity of purified cyclooxygnase enzyme (COX-1 or COX-2). According to manufacturer instructions, purified enzyme, heme and test extracts can be mixed in assay buffer and incubated with shaking for 15 min at room temperature. Following incubation, arachidonic acid and colorimetric substrate can be added to initiate the reaction. Color progression can be evaluated by colorimetric plate reading at 590 nm. The percent inhibition of COX-1 or COX-2 activity can be calculated compared to non-treated controls to determine the ability of test extracts to inhibit the activity of purified enzyme.

Lipoxygenase (LO) Assay:

An in vitro lipoxygenase (LO) inhibition assay. LOs are non-heme iron-containing dioxygenases that catalyze the addition of molecular oxygen to fatty acids. Linoleate and arachidonate are the main substrates for LOs in plants and animals. Arachadonic acid may then be converted to hydroxyeicosotrienenoic (HETE) acid derivatives, that are subsequently converted to leukotrienes, potent inflammatory mediators. This assay provides an accurate and convenient method for screening lipoxygenase inhibitors by measuring the hydroperoxides generated from the incubation of a lipoxygenase (5-, 12-, or 15-LO) with arachidonic acid. The Colorimetric LO Inhibitor screening kit (#760700, Cayman Chemical) can be used to determine the ability of each of the active ingredients, any one of the combination of ingredients, or compositions having said combinations disclosed in the specification to inhibit enzyme activity. Purified 15-lipoxygenase and test ingredients can be mixed in assay buffer and incubated with shaking for 10 min at room temperature. Following incubation, arachidonic acid can be added to initiate the reaction and the mixtures can be incubated for an additional 10 min at room temperature. Colorimetric substrate can be added to terminate catalysis and color progression can be evaluated by fluorescence plate reading at 490 nm. The percent inhibition of lipoxyganse activity can be calculated compared to non-treated controls to determine the ability of each of the active ingredients, any one of the combination of ingredients, or compositions having said combinations disclosed in the specification to inhibit the activity of purified enzyme.

Elastase Assay:

EnzChek® Elastase Assay (Kit # E-12056) from Molecular Probes (Eugene, Oreg. USA) can be used as an in vitro enzyme inhibition assay for measuring inhibition of elastase activity for each of the active ingredients, any one of the combination of ingredients, or compositions having said combinations disclosed in the specification. The EnzChek kit contains soluble bovine neck ligament elastin that can be labeled with dye such that the conjugate's fluorescence can be quenched. The non-fluorescent substrate can be digested by elastase or other proteases to yield highly fluorescent fragments. The resulting increase in fluorescence can be monitored with a fluorescence microplate reader. Digestion products from the elastin substrate have absorption maxima at ~505 nm and fluorescence emission maxima at ~515 nm. The peptide, N-methoxysuccinyl-Ala-Ala-Pro-Val-chloromethyl ketone, can be used as a selective, collective inhibitor of elastase when utilizing the EnzChek Elastase Assay Kit for screening for elastase inhibitors.

Oil Control Assay:

An assay to measure reduction of sebum secretion from sebaceous glands and/or reduction of sebum production from sebaceous glands can be assayed by using standard techniques known to those having ordinary skill in the art. In some aspects, the forehead can be used. Each of the active ingredients, any one of the combination of ingredients, or compositions having said combinations disclosed in the specification can be applied to one portion of the forehead once or twice daily for a set period of days (e.g., 1, 2, 3, 4, 5, 6, 7, 8, 9, 10, 11, 12, 13, 14, or more days), while another portion of the forehead is not treated with the composition. After the set period of days expires, then sebum secretion can be assayed by application of fine blotting paper to the treated and untreated forehead skin. This is done by first removing any sebum from the treated and untreated areas with moist and dry cloths. Blotting paper can then be applied to the treated and untreated areas of the forehead, and an elastic band can be placed around the forehead to gently press the blotting paper onto the skin. After 2 hours the blotting papers can be removed, allowed to dry and then transilluminated. Darker blotting paper correlates with more sebum secretion (or lighter blotting paper correlates with reduced sebum secretion.

Erythema Assay:

An assay to measure the reduction of skin redness can be evaluated using a Minolta Chromometer. Skin erythema may be induced by applying a 0.2% solution of sodium dodecyl sulfate on the forearm of a subject. The area is protected by an occlusive patch for 24 hrs. After 24 hrs, the patch is removed and the irritation-induced redness can be assessed using the a* values of the Minolta Chroma Meter. The a* value measures changes in skin color in the red region. Immediately after reading, the area is treated with the active ingredients, any one of the combination of ingredients, or compositions having said combinations disclosed in the specification. Repeat measurements can be taken at regular intervals to determine the formula's ability to reduce redness and irritation.

Skin Clarity and Reduction in Freckles and Age Spots Assay:

Skin clarity and the reduction in freckles and age spots can be evaluated using a Minolta Chromometer. Changes in skin color can be assessed to determine irritation potential due to product treatment using the a* values of the Minolta Chroma Meter. The a* value measures changes in skin color in the red region. This is used to determine whether each of the active ingredients, any one of the combination of ingredients, or compositions having said combinations disclosed in the specification is inducing irritation. The measurements can be made on each side of the face and averaged, as left and right facial values. Skin clarity can also be measured using the Minolta Meter. The measurement is a combination of the a*, b, and L values of the Minolta Meter and is related to skin brightness, and correlates well with skin smoothness and hydration. Skin reading is taken as above. In one non-limiting aspect, skin clarity can be described as L/C where C is chroma and is defined as $(a^2+b^2)^{1/2}$ Skin Dryness, Surface Fine Lines, Skin Smoothness, and Skin Tone Assay:

Skin dryness, surface fine lines, skin smoothness, and skin tone can be evaluated with clinical grading techniques. For example, clinical grading of skin dryness can be determined by a five point standard Kligman Scale: (0) skin is soft and moist; (1) skin appears normal with no visible dryness; (2) skin feels slightly dry to the touch with no visible flaking; (3) skin feels dry, tough, and has a whitish appearance with some scaling; and (4) skin feels very dry, rough, and has a whitish appearance with scaling. Evaluations can be made independently by two clinicians and averaged.

Clinical Grading of Skin Tone Assay:

Clinical grading of skin tone can be performed via a ten point analog numerical scale: (10) even skin of uniform, pinkish brown color. No dark, erythremic, or scaly patches upon examination with a hand held magnifying lens. Microtexture of the skin very uniform upon touch; (7) even skin tone observed without magnification. No scaly areas, but slight discolorations either due to pigmentation or erythema. No discolorations more than 1 cm in diameter; (4) both skin discoloration and uneven texture easily noticeable. Slight scaliness. Skin rough to the touch in some areas; and (1) uneven skin coloration and texture. Numerous areas of scaliness and discoloration, either hypopigmented, erythremic or dark spots. Large areas of uneven color more than 1 cm in diameter. Evaluations were made independently by two clinicians and averaged.

Clinical Grading of Skin Smoothness Assay:

Clinical grading of skin smoothness can be analyzed via a ten point analog numerical scale: (10) smooth, skin is moist and glistening, no resistance upon dragging finger across surface; (7) somewhat smooth, slight resistance; (4) rough, visibly altered, friction upon rubbing; and (1) rough, flaky, uneven surface. Evaluations were made independently by two clinicians and averaged.

Skin Smoothness and Wrinkle Reduction Assay with Methods Disclosed in Packman et al. (1978):

Skin smoothness and wrinkle reduction can also be assessed visually by using the methods disclosed in Packman et al. (1978). For example, at each subject visit, the depth, shallowness and the total number of superficial facial lines (SFLs) of each subject can be carefully scored and recorded. A numerical score was obtained by multiplying a number factor times a depth/width/length factor. Scores are obtained for the eye area and mouth area (left and right sides) and added together as the total wrinkle score.

Skin Firmness Assay with a Hargens Ballistometer:

Skin firmness can be measured using a Hargens ballistometer, a device that evaluates the elasticity and firmness of the skin by dropping a small body onto the skin and recording its first two rebound peaks. The ballistometry is a small lightweight probe with a relatively blunt tip (4 square mm-contact area) was used. The probe penetrates slightly into the skin and results in measurements that are dependent upon the properties of the outer layers of the skin, including the stratum corneum and outer epidermis and some of the dermal layers.

Skin Softness/Suppleness Assay with a Gas Bearing Electrodynamometer:

Skin softness/suppleness can be evaluated using the Gas Bearing Electrodynamometer, an instrument that measures the stress/strain properties of the skin. The viscoelastic properties of skin correlate with skin moisturization. Measurements can be obtained on the predetermined site on the cheek area by attaching the probe to the skin surface with double-stick tape. A force of approximately 3.5 gm can be applied parallel to the skin surface and the skin displacement is accurately measured. Skin suppleness can then be calculated and is expressed as DSR (Dynamic Spring Rate in gm/mm).

Appearance of Lines and Wrinkles Assay with Replicas:

The appearance of lines and wrinkles on the skin can be evaluated using replicas, which is the impression of the skin's surface. Silicone rubber like material can be used. The replica can be analyzed by image analysis. Changes in the visibility of lines and wrinkles can be objectively quantified via the taking of silicon replicas form the subjects' face and analyzing the replicas image using a computer image analysis system. Replicas can be taken from the eye area and the neck area, and photographed with a digital camera using a low angle incidence lighting. The digital images can be analyzed with an image processing program and are of the replicas covered by wrinkles or fine lines was determined.

Surface Contour of the Skin Assay with a Profilometer/Stylus Method:

The surface contour of the skin can be measured by using the profilometer/Stylus method. This includes either shining a light or dragging a stylus across the replica surface. The vertical displacement of the stylus can be fed into a computer via a distance transducer, and after scanning a fixed length of replica a cross-sectional analysis of skin profile can be generated as a two-dimensional curve. This scan can be repeated any number of times along a fix axis to generate a simulated 3-D picture of the skin. Ten random sections of the replicas using the stylus technique can be obtained and combined to generate average values. The values of interest include Ra which is the arithmetic mean of all roughness (height) values computed by integrating the profile height relative to the mean profile height. Rt which is the maximum vertical distance between the highest peak and lowest trough, and Rz which is the mean peak amplitude minus the mean peak height. Values are given as a calibrated value in mm. Equipment should be standardized prior to each use by scanning metal standards of know values. Ra Value can be computed by the following equation: Ra=Standardize roughness; $l_m$=the traverse (scan) length; and y=the absolute value of the location of the profile relative to the mean profile height (x-axis).

MELANODERM™ Assay:

In other non-limiting aspects, the efficacy of each of the active ingredients, any one of the combination of ingredients, or compositions having said combinations disclosed in the specification can be evaluated by using a skin analog, such as, for example, MELANODERM™. Melanocytes, one of the cells in the skin analog, stain positively when exposed to L-dihydroxyphenyl alanine (L-DOPA), a precursor of melanin. The skin analog, MELANODERM™, can be treated with a variety of bases containing each of the active ingredients, any one of the combination of ingredients, or compositions having said combinations disclosed in the specification or with the base alone as a control. Alternatively, an untreated sample of the skin analog can be used as a control.

Production of Hyaluronic Acid—

Changes in the production of hyaluronic acid in human dermal fibroblasts due to each of the active ingredients, any one of the combination of ingredients, or compositions having said combinations disclosed in the specification can be measured. HA is a polysaccharide involved in stabilization of the structure of the matrix and is involved in providing turgor pressure to tissue and cells. As one non-limiting example, HA production in treated and non-treated adult human dermal fibroblasts (HDFa) cells can be determined using the Hyaluronan DuoSet ELISA kit from R&D Systems (DY3614). In this assay, for production of samples, subconfluent HDFa cells from Cascade Biologics (C-13-5C) are incubated at 37° C. and 10% C02 in starvation medium (0.15% fetal bovine serum and 1% Penicillin Streptomycin solution in Dulbecco's Modified Eagle Medium) for 72 hours prior to treatment. The cells are then incubated with fresh starvation medium with either test compound, positive control (phorbol 12-myristate 13-acetate from Sigma-Aldrich (P1585) and platelet derived growth factor from Sigma-Aldrich (P3201)), or no additive for 24 hours. Media is then collected and frozen at −80° C. until use in the ELISA assay.

Briefly, the ELISA assay employs a quantitative sandwich enzyme immunoassay technique whereby a capture antibody specific for HA can be pre-coated onto a microplate. Standards and media from treated and untreated cells are pipetted into the microplate wells to enable any HA present to be bound by the immobilized antibody. After washing away any unbound substances, an enzyme-linked detection antibody specific for HA is added to the wells. Following a wash to remove any unbound antibody-enzyme reagent, a substrate solution is added to the wells to allow color development in proportion to the amount of HA bound in the initial step. The color development is stopped at a specific time and the intensity of the color at 450 nm can be measured using a microplate reader.

Inhibition of Hyaluronidase Activity—

Changes in the activity of hyaluronidase due to each of the active ingredients, any one of the combination of ingredients, or compositions having said combinations disclosed in the specification can be measured. Hyaluronidase is an enzyme that degrades HA. HA is a polysaccharide involved in stabilization of the structure of the matrix and is involved in providing turgor pressure to tissue and cells. As one non-limiting example, hyaluronidase activity can be determined using an in vitro protocol modified from Sigma-Aldrich protocol # EC 3.2.1.35. Briefly, hyaluronidase type 1-S from Sigma-Aldrich (H3506) is added to microplate reaction wells containing test compound or controls. Tannic acid can be used as a positive control inhibitor, no test compound can be added for the control enzyme, and wells with test compound or positive control but without hyaluronidase can be used as a background negative control. The wells are incubated at 37° C. for 10 minutes before addition of substrate (HA). Substrate is added and the reactions incubated at 37° C. for 45 minutes. A portion of each reaction solution is then transferred to and gently mixed in a solution of sodium acetate and acetic acid pH 3.75 to stop that portion of the reaction (stopped wells). The stopped wells and the reaction wells should both contain the same volume of solution after addition of the portion of the reaction solution to the stopped wells. Both the reaction wells and the stopped wells are incubated for 10 minutes at room temperature. Absorbance at 600 nm is then measured for both the reaction wells and the stopped wells. Inhibition can be calculated using the following formulas: Inhibitor (or control) activity=(Inhibitor stopped wells absorbance at 600 nm−inhibitor reaction wells absorbance at 600 nm); Initial activity=control enzyme absorbance at 600 nm; Percent Inhibition=[(Initial activity/Inhibitor Activity)*100]−100.

Peroxisome Proliferator-Activated Receptor Gamma (PPAR-γ) Activity—

Changes in the activity of PPAR-γ due to each of the active ingredients, any one of the combination of ingredients, or compositions having said combinations disclosed in the specification can be measured. PPAR-γ is a receptor critical for the production of sebum. As one non-limiting example, the activity of PPAR-γ can be determined using a bioassay that analyzes the ability of a test compound or composition to inhibit binding of a ligand. Briefly, fluorescent small-molecule pan-PPAR ligand, FLUORMONE™ Pan-PPAR Green, available from Life Technologies (PV4894), can be used to determine if test compounds or compositions are able to inhibit binding of the ligand to PPAR-γ. The samples wells include PPAR-γ and fluorescent ligand and either: test compound or composition (test); a reference inhibitor, rosiglitazone (positive control); or no test compound (negative control). The wells are incubated for a set period of time to allow the ligand opportunity to bind the PPAR-γ. The fluorescence polarization of each sample well can then be measured and compared to the negative control well to determine the percentage of inhibition by the test compound or composition.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Cosmetic Ingredient Dictionary, Third Edition, CTFA, 1982
International Cosmetic Ingredient Dictionary, Fourth edition, CTFA, 1991
International Cosmetic Ingredient Dictionary and Handbook, Tenth Edition, CTFA, 2004
International Cosmetic Ingredient Dictionary and Handbook, Twelfth Edition, CTFA, 2008

The invention claimed is:

1. A method of treating a human with erythemic skin, the method comprising topically applying to said human a composition comprising:
   0.0001% to 5% w/w of a hydrolyzed algae extract;
   0.0001% to 5% w/w of a saccharide isomerate;
   at least one of octinoxate, homosalate, oxybenzone, octisalate, avobenzone, octocrylene, titanium dioxide, and zinc oxide; and
   a dermatologically acceptable vehicle,
wherein at least one of skin permeability is decreased, filaggrin production is increased, skin moisture is increased, occludin production is increased, or TNF-a production is inhibited in the skin, wherein the hydrolyzed algae extract comprises exopolysaccharides from Halymenia durvillei, and wherein the saccharide isomerate comprises an exopolysaccharide synthesized by Vibrio alginolyticus.

2. The method of claim 1, wherein the hydrolyzed algae extract increases production of filaggrin, increases skin moisture, increases production of occludin, or decreases skin permeability in the skin.

3. The method of claim 1, wherein the saccharide isomerate increases production of filaggrin, increases skin moisture, increases production of occludin, or inhibits TNF-α production in the skin.

4. The method of claim 1, wherein the composition is formulated as at least one of a moisturizer, a mask, a foundation, a freshener, or a cleanser.

5. The method of claim 1, wherein the composition further comprises 35% to 98% w/w of water.

6. The method of claim 1, wherein the skin permeability is decreased in the skin.

7. The method of claim 1, wherein filaggrin production is increased in the skin.

8. The method of claim 1, wherein skin moisture is increased in the skin.

9. The method of claim 1, wherein occludin production is increased in the skin.

10. The method of claim 1, wherein TNF-α production is decreased in the skin.

* * * * *

UNITED STATES PATENT AND TRADEMARK OFFICE
CERTIFICATE OF CORRECTION

PATENT NO. : 10,869,821 B2
APPLICATION NO. : 16/232723
DATED : December 22, 2020
INVENTOR(S) : Carle et al.

It is certified that error appears in the above-identified patent and that said Letters Patent is hereby corrected as shown below:

In the Claims

In Claim 1, Column 39, Line 16 replace "human" with "human skin" therefore

Signed and Sealed this
Twenty-fourth Day of August, 2021

Drew Hirshfeld
*Performing the Functions and Duties of the*
*Under Secretary of Commerce for Intellectual Property and*
*Director of the United States Patent and Trademark Office*